United States Patent
Ishikawa et al.

(10) Patent No.: US 8,258,162 B2
(45) Date of Patent: Sep. 4, 2012

(54) CATECHOL DERIVATIVE, PHARMACEUTICAL COMPOSITION CONTAINING THE SAME, USE OF THE CATECHOL DERIVATIVE, AND USE OF THE PHARMACEUTICAL COMPOSITION

(75) Inventors: Takehiro Ishikawa, Azumino (JP); Satoko Kobayashi, Azumino (JP); Hitoshi Inoue, Azumino (JP); Yasunori Ueno, Azumino (JP); Masako Yoshida, Azumino (JP); Nobuyuki Tanaka, Azumino (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 54 days.

(21) Appl. No.: 13/002,475

(22) PCT Filed: Jun. 26, 2009

(86) PCT No.: PCT/JP2009/061685
§ 371 (c)(1),
(2), (4) Date: Feb. 2, 2011

(87) PCT Pub. No.: WO2010/001821
PCT Pub. Date: Jan. 7, 2010

(65) Prior Publication Data
US 2011/0172208 A1 Jul. 14, 2011

(30) Foreign Application Priority Data
Jul. 4, 2008 (JP) .................................. 2008-175567

(51) Int. Cl.
A61K 31/04 (2006.01)
A61K 31/426 (2006.01)
A61K 31/42 (2006.01)
A61K 31/381 (2006.01)
C07C 205/06 (2006.01)
C07D 277/20 (2006.01)
C07D 261/06 (2006.01)
C07D 333/02 (2006.01)

(52) U.S. Cl. ........ 514/365; 548/202; 548/247; 514/378; 514/438; 514/579; 549/70; 560/20

(58) Field of Classification Search ............... 548/333.5, 548/202, 247; 514/399, 365, 378, 438, 579; 549/70; 560/20
See application file for complete search history.

(56) References Cited

U.S. PATENT DOCUMENTS
2002/0037931 A1 3/2002 Learmonth et al.

FOREIGN PATENT DOCUMENTS
JP 2004-501129 A 1/2004
JP 2008-308494 A 12/2008

OTHER PUBLICATIONS

Victor Behar, et al., "Total Synthesis of the Novel Benzopentathiepin Varacinium Trifluoroacetate: The Viability of 'Varacin Free Base'", Journal of American Chemical Society, 1993, pp. 7017-7018, vol. 115.*
S. V. Eswaran, et al., "The Unusual Formation of Methyl u,-(5,6-Dimenthoxycarbonyl-2-3-Dimethoxyazepin-7-ylidene)-u,-[5-methoxycarbonyl-2-3-Dimethoxypyrid-6-yl) acetate During the Pyrolysis of 'Azido-meta-hemipinate'", Journal of Heterocyclic Chemistry, 1996, pp. 1333-1337, vol. 33, No. 4.*
S. V. Eswaran, et al., "The Unusual Formation of Methyl α-(5,6-Dimenthoxycarbonyl-2-3-Dimethoxyazepin-7-ylidene)-α-[5-methoxycarbonyl-2-3-Dimethoxypyrid-6-yl) acetate During the Pyrolysis of 'Azido-meta-hemipinate'", Journal of Heterocyclic Chemistry, 1996, pp. 1333-1337, vol. 33, No. 4.
International Search Report of PCT/JP2009/061685 dated Jul. 28, 2009.

* cited by examiner

Primary Examiner — Rebecca Anderson
Assistant Examiner — Samantha Shterengarts
(74) Attorney, Agent, or Firm — Sughrue Mion, PLLC

(57) ABSTRACT

The present invention provides compounds represented by general formula (I):

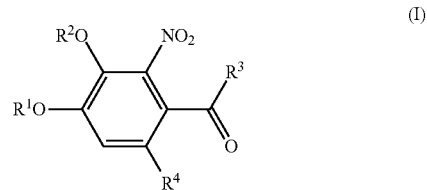

or pharmaceutical acceptable salts thereof, wherein $R^1$ and $R^2$ are each hydrogen, lower acyl, lower alkoxycarbonyl or the like; $R^3$ is lower alkyl, halo-lower alkyl, cycloalkyl, heterocycloalkyl, optionally substituted aryl, optionally substituted heteroaryl or the like; $R^4$ is cyano, lower alkoxycarbonyl, carboxy or the like, which exhibit potent COMT inhibitory activities. The present invention also provides pharmaceutical compositions containing said compound, and uses thereof.

8 Claims, No Drawings

CATECHOL DERIVATIVE, PHARMACEUTICAL COMPOSITION CONTAINING THE SAME, USE OF THE CATECHOL DERIVATIVE, AND USE OF THE PHARMACEUTICAL COMPOSITION

CROSS REFERENCE TO RELATED APPLICATIONS

This is a National Stage of International Application No. PCT/JP2009/061685 filed Jun. 26, 2009, which claims priority from Japanese Patent Application No. 2008-175567 filed on Jul. 4, 2008, the contents of all of which are incorporated herein by reference in their entirety.

TECHNICAL FIELD

The present invention relates to novel catechol derivatives, which exhibit catechol-O-methyltrasferase inhibitory activities, pharmaceutical compositions containing the same, and their uses.

BACKGROUND ART

Parkinson's disease is a progressive neurodegenerative disease which usually affects elderly patients. The number of parkinsonian patients is growing with progressive aging of society. Parkinson's disease is characterized by impairment in coordinated motor function such as rest tremor, rigidity, akinesia, postural instability and the like. It is thought that Parkinson's disease results from deficiency of dopamine in the striatum, which is caused by degeneration of dopamine neuron in the substantia nigra. For that reasons, L-dopa or dopamine receptor stimulants are used for the treatment of Parkinson's disease.

L-dopa is a precursor of dopamine, and is metabolized to dopamine which exerts its efficacy in the brain. Since L-dopa has a very short serum half-life, L-dopa is administered usually in combination with a peripheral aromatic L-amino acid decarboxylase inhibitor and/or a catechol-O-methyltrasferase inhibitor, which inhibit the metabolism of L-dopa in the body. Catechol-O-methyltrasferase (thereinafter referred to as "COMT") is an enzyme that catalyze the transfer of the methyl group of S-adenosyl-L-methionine to chatechol substrates. The inhibition of the COMT enzyme slows down the metabolism of L-dopa to 3-O-methyl-L-dopa, which results in the significant increase in serum half-life of L-dopa and the amount of L-dopa crossing the blood-brain-barrier. In this way, a COMT inhibitor, when administered in combination with L-dopa, increases the bioavailability of L-dopa and prolongs its effects (see Non Patent Literature 1).

COMT inhibitors are also expected to be useful for treating or preventing hypertension since COMT inhibitors exhibit urinary sodium excretion promoting activities (see Non Patent Literature 2). COMT inhibitors are also expected to be useful for treating or preventing depression (see Non Patent Literature 3).

A variety of COMT inhibitors have been reported recently. Among them, tolcopone (3,4-dihydroxy-4'-methyl-5-nitrobenzophenone, Patent Literature 1) and entacapone ((E)-2-cyano-N,N-diethyl-3-(3,4-dihydroxy-5-nitrophenyl) acrylamide, Patent Literature 2) are the most potent COMT inhibitors known to date. Tolcopone or entacapone are clinically administered to patients for treating Parkinson's disease. However, it has been reported that tolcapone causes severe liver function damage, and can only be used in parkinsonian patients strictly with regular monitoring of liver function (see Non Patent Literature 4). On the other hand, entacapone has less potent efficacy than tolcapone, and has a problem to have a very limited duration of effect (see Non Patent Literature 5). Accordingly, there is still a need for novel COMT inhibitors with potent COMT inhibitory activities and a desirable safety profile.

Patent Literature 3 discloses substituted nitrocatechol derivatives such as carbonic acid 4,5-dibenzoyl-2-ethoxycarbonyloxy-3-nitrophenyl ester ethyl ester; (6-benzoyl-3,4-dihydroxy-2-nitrophenyl)phenylmethanone; 3,4-dihydroxy-2-nitrophenyl)phenylmethanone and the like, which have COMT inhibitory activities (see examples 4 and 61 in Patent Literature 3). However, the results of table 2 in Patent Literature 3 show that the liver COMT inhibitory activities of these compounds are less potent as compared with that of entacapone.

CITATION LIST

Patent Literature

1. Publication of Unexamined Application of European Patent Specification No. 237929
2. Publication of Unexamined Application of British Patent Specification No. 2200109
3. International Publication pamphlet No. WO2001/98250

Non Patent Literature

1. Nutt J. G. et al, "Lancet", 1998, vol. 351, No. 9111, p. 1221-1222
2. Eklof A. C. et al, "Kidney Int.", 1997, vol. 52, No. 3, p. 742-747
3. Moreau J. L. et al, "Behan. Pharmacol.", 1994, vol. 5, No. 3, p. 344-350
4. Benabou R. et al, "Expert Opin. Drug Saf.", 2003, vol. 2, No. 3, p. 263-267
5. ForsbergM. et al, "J. Pharmacol. Exp. Ther.", 2003, vol. 304, No. 2, p. 498-506
6. KogaK. et al, "Eur. J. Pharmacol.", 2000, vol. 408, p. 249-255

DISCLOSURE OF THE INVENTION

An object of the present invention is to provide a novel compound having potent COMT inhibitory activities, and more preferably possessing a desirable safety profile.

The inventors of the present invention diligently worked to achieve the foregoing object and found that catechol derivatives represented by general formula (I) show excellent COMT inhibitory activities and possess high safety. Based on these findings, the present invention has been accomplished.

The present invention therefore provides a compound represented by general formula (I):

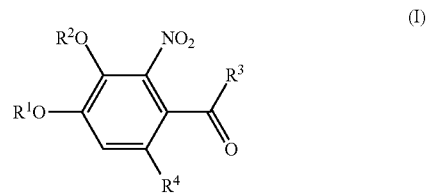

or a pharmaceutically acceptable salt thereof, wherein

R$^1$ and R$^2$ are each independently a hydrogen atom, a lower acyl group, a lower alkoxycarbonyl group or —C(O)NR$^{11}$R$^{12}$, or R$^1$ and R$^2$ are joined together to form —C(O)—;

R$^3$ is:
  a) a lower alkyl group,
  b) a halo-lower alkyl group,
  c) a cycloalkyl group,
  d) a hydroxycycloalkyl group,
  e) a heterocycloalkyl group,
  f) an aryl group, wherein the ring of the aryl group is unsubstituted or substituted with 1 to 5 substituents independently selected from the group consisting of a halogen atom, a lower alkyl group, a halo-lower alkyl group, a cyano group, a lower acyl group, a lower alkoxy group, a hydroxy group and a lower alkoxycarbonyl group,
  g) a heteroaryl group, wherein the ring of the heteroaryl group is unsubstituted or substituted with 1 to 3 substituents independently selected from the group consisting of a halogen atom, a lower alkyl group, a halo-lower alkyl group, a lower alkoxy group and a hydroxy group,
  h) an aralkyl group, wherein the ring of the aralkyl group is unsubstituted or substituted with 1 to 5 substituents independently selected from the group consisting of a halogen atom, a lower alkyl group, a halo-lower alkyl group and a lower alkoxy group,
  i) a lower alkoxy group,
  j) a halo-lower alkoxy group,
  k) a lower alkoxy-lower alkoxy group,
  l) a cycloalkyloxy group, or
  m) —NR$^{11}$R$^{12}$;

R$^4$ is:
  a) a cyano group,
  b) a lower alkoxycarbonyl group,
  c) a halo-lower alkoxycarbonyl group,
  d) a lower alkoxy-lower alkoxycarbonyl group,
  e) a cycloalkyloxycarbonyl group, or
  f) a carboxy group;

R$^{11}$ and R$^{12}$ are each independently a hydrogen atom, a lower alkyl group, a cycloalkyl group, a phenyl group or an aralkyl group, or R$^{11}$ and R$^{12}$, together with the nitrogen atom to which they are bonded, form a cyclic amino group.

In another aspect, the present invention provides a pharmaceutical composition which comprises, as an active ingredient, a compound of general formula (I) or a pharmaceutically acceptable salt thereof.

In still another aspect, the present invention provides a catechol-O-methyltransferase inhibitor which comprises, as an active ingredient, a compound of general formula (I) or a pharmaceutically acceptable salt thereof.

In still another aspect, the present invention provides a pharmaceutical combination which comprises a compound of general formula (I) or a pharmaceutically acceptable salt thereof and at least one selected from L-dopa or an aromatic L-amino acid decarboxylase inhibitor.

In still another aspect, the present invention provides a therapeutic or prophylactic agent for Parkinson's disease, depression or hypertension which comprises, as an active ingredient, a compound of general formula (I) or a pharmaceutically acceptable salt thereof.

In still another aspect, the present invention provides a use of a compound represented by general formula (I) or a pharmaceutically acceptable salt thereof for the manufacture of a medicament for treating or preventing Parkinson's disease, depression or hypertension.

In still another aspect, the present invention provides a method for treating or preventing Parkinson's disease, depression or hypertension which comprises administering an effective amount of a compound represented by general formula (I) or a pharmaceutically acceptable salt thereof.

Advantageous Effects of Invention

Compounds of the present invention exhibit potent COMT inhibitory activities. Moreover, compounds of the present invention have a desirable safety profile since compounds of the present invention have extremely slight hepatotoxicity. Accordingly, compounds of the present invention are useful as a therapeutic or prophylactic agent for Parkinson's disease, depression or hypertension. Especially, compounds of the present invention are useful as a therapeutic or prophylactic agent for Parkinson's disease since use of compounds of the present invention in combination with L-dopa increases the bioavailability of L-dopa remarkably.

DESCRIPTION OF EMBODIMENTS

The invention is described using the terms defined below unless otherwise specified.

The term "lower" herein denotes residues with 1 to 6 carbon atoms unless otherwise specified.

The term "halogen atom" refers to a fluorine, chlorine, bromine or iodine atom.

The term "lower alkyl group" refers to a straight chained or branched C$_{1-6}$ alkyl group such as a methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl group and the like.

The term "halo-lower alkyl group" refers to a C$_{1-6}$ alkyl group substituted with the same or different 1 to 3 halogen atoms such as a fluoromethyl, difluoromethyl, trifluoromethyl, 2,2,2-trifluoroethyl group and the like, preferably a difluoromethyl or trifluoromethyl group.

The term "cycloalkyl group" refers to a 3- to 7-membered saturated cyclic hydrocarbon such as a cyclopropyl, cyclobutyl, cyclopentyl, cyclohexyl and cycloheptyl group.

The term "hydroxycycloalkyl group" refers to a 3- to 7-membered saturated cyclic hydrocarbon substituted with a hydroxy group such as a 3-hydroxycyclopentyl, 2-hydroxycyclohexyl, 3-hydroxycyclohexyl, 4-hydroxycyclohexyl group and the like.

The term "heterocycloalkyl group" refers to a 4- to 7-membered saturated heterocyclic group which contains —NH—, —O— or —S— as a member of the ring and is bonded via a carbon atom. Examples of heterocycloalkyl groups include a tetrahydrofuryl, tetrahydrothienyl, tetrahydropyranyl, pyrrolidin-2-yl, pyrrolidin-3-yl, piperidin-2-yl, piperidin-3-yl, piperidin-4-yl group and the like.

The term "aryl group" refers to a C$_{6-10}$ aromatic hydrocarbon group such as a phenyl, 1-naphtyl and 2-naphthyl group, preferably a phenyl group.

The term "aralkyl group" refers to an aryl-C$_{1-6}$ alkyl group such as a benzyl, phenethyl, 1-phenylethyl, 3-phenylpropyl, 4-phenylbutyl, naphthylmethyl group and the like.

The term "heteroaryl group" refers to a 5- or 6-membered monocyclic aromatic heterocycle having 1 to 5 carbon atoms and to 4 heteroatoms selected independently from the group consisting of an oxygen, nitrogen and sulfur atom, or a 8- to 10-membered bicyclic aromatic heterocycle having 1 to 9 carbon atoms and 1 to 4 heteroatoms selected independently from the group consisting of an oxygen, nitrogen and sulfur atom, provided that said heterocycles do not include adjacent oxygen and/or sulfur atoms. Examples of monocyclic heteroaryl groups include pyrrolyl, furyl, thienyl, imidazolyl, pyrazolyl, oxazolyl, isoxazolyl, 1,2,4-oxadiazolyl, tetrazolyl, thiazolyl, isothiazolyl, 1,2,3-thiadiazolyl, triazolyl, pyridyl, pyrazinyl, pyrimidyl and pyridazinyl, preferably thienyl, isoxazolyl or thiazolyl. Examples of bicyclic heteroaryl groups include indolyl, indazolyl, benzofuranyl, benzothienyl, benzothiazolyl, quinolyl, isoquinolyl, phthalazinyl, benzimidazolyl, benzoxazolyl and the like. The heterocycles include all position isomers such as 2-pyridyl, 3-pyridyl or 4-pyridyl.

The term "lower acyl group" refers to a ($C_{1-6}$ alkyl)-CO-group such as an acetyl, propionyl, butyryl, isobutyryl, pivaloyl, valeryl, isovaleryl group and the like.

The term "lower alkoxy group" refers to a straight chained or branched $C_{1-6}$ alkoxy group such as a methoxy, ethoxy, propoxy, isopropoxy, butoxy isobutoxy, sec-butoxy, tert-butoxy, pentyloxy, hexyloxy group and the like.

The term "halo-lower alkoxy group" refers to a $C_{1-6}$ alkoxy group substituted with the same or different 1 to 3 halogen atoms such as a difluoromethoxy, trifluoromethoxy, 2,2,2-trifluoro-ethoxy group and the like.

The term "lower alkoxy-lower alkoxy group" refers to a $C_{1-6}$ alkoxy-$C_{1-6}$ alkoxy group such as a 2-methoxyethoxy, 2-ethoxyethoxy, 3-methoxypropoxy, 4-methoxybutoxy group and the like.

The term "cycloalkyloxy group" refers to a (cycloalkyl)-O-group such as a cyclopropyloxy, cyclobutyloxy, cyclopentyloxy, cyclohexyloxy and the like.

The term "lower alkoxycarbonyl group" refers to a ($C_{1-6}$ alkoxy)-C(O)— group such as a methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl group and the like.

Preferred lower alkoxycarbonyl groups for $R^4$ are a methoxycarbonyl, ethoxycarbonyl or isopropoxycarbonyl group, and more preferably a methoxycarbonyl or ethoxycarbonyl group.

The term "halo-lower alkoxycarbonyl group" refers to a (halo-$C_{1-6}$ alkoxy)-C(O)— group such as 2,2,2-trifluoroethyl-oxycarbonyl, 2,2,2-trichloroethyloxycarbonyl and the like.

The term "cycloalkyloxycarbonyl group" refers to a (cycloalkyl)-O—C(O)— group such as a cyclopentyloxycarbonyl, cyclohexyloxycarbonyl group and the like.

Ther term "lower alkoxy-lower alkoxycarbonyl group" refers to a ($C_{1-6}$ alkoxy-$C_{1-6}$ alkoxy)-C(O)— group such as a 2-methoxyethoxycarbonyl, 2-ethoxyethoxycarbonyl, 3-methoxy-propoxycarbonyl group and the like.

The term "cyclic amino group" refers to a 5- to 7-membered saturated cyclic amine which may contain —NH—, —O— or —S— as a member of the ring. Examples of cyclic amino groups include a 1-pyrrolidyl, piperidino, piperazino, morpholino, thiomorpholino group. The cyclic amino group may be optionally substituted with one or two alkyl group or a lower alkoxycarbonyl group such as a 4-ethoxycarbonylpiperazino, 4-methylcarbonyl-piperazino group and the like.

In the case where a compound represented by general formula (I) contains one or more asymmetric carbons, then all stereoisomers in the R- or S-configuration at each of asymmetric carbons and their mixture are contemplated within the scope of the present invention. In such cases, racemic compounds, racemic mixtures, individual enantiomers and mixtures of diastereomers are also contemplated within the scope of the present invention.

In the case where a compound represented by general formula (I) exists in one or more geometrical isomers, then all geometrical isomers are also contemplated within the scope of the present invention.

In the case where a compound represented by general formula (I) exists in one or more atrop-isomers, then all atrop-isomers are also contemplated within the scope of the present invention.

A compound represented by general formula (I) may form a solvate with a pharmaceutically acceptable solvent such as water, ethanol and the like.

Compounds represented by general formula (I) may exist in the form of salts. Examples of such salts include acid addition salts formed with mineral acids such as hydrochloric acid, hydrobromic acid, hydroiodic acid, sulfuric acid, nitric acid, phosphoric acid and the like; acid addition salts formed with organic acids such as formic acid, acetic acid, trifluoroacetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, glutamic acid, aspartic acid and the like; basic salts formed with inorganic bases such as sodium, potassium, magnesium, calcium and the like; basic salts formed with organic bases such as triethylamine, piperidine, morpholine, lysine and the like.

In an embodiment of a compound represented by general formula (I) of the present invention,
preferably $R^1$ and $R^2$ are a hydrogen atom;
$R^3$ is preferably:
  a) a lower alkyl group,
  b) a halo-lower alkyl group,
  c) a cycloalkyl group,
  d) a heterocycloalkyl group,
  e) an aryl group, wherein the ring of the aryl group is unsubstituted or substituted with 1 to 5 substituents independently selected from the group consisting of a halogen atom, a lower alkyl group, a halo-lower alkyl group, a cyano group, a lower acyl group, a lower alkoxy group and a lower alkoxycarbonyl group,
  f) a heteroaryl group, wherein the ring of the heteroaryl group is unsubstituted or substituted with 1 to 3 substituents independently selected from the group consisting of a halogen atom, a lower alkyl group, a halo-lower alkyl group and a lower alkoxy group,
  g) an aralkyl group, wherein the ring of the aralkyl group is unsubstituted or substituted with 1 to 5 substituents independently selected from the group consisting of a halogen atom, a lower alkyl group, a halo-lower alkyl group and a lower alkoxy group,
  h) a lower alkoxy group, or
  i) —$NR^{11}R^{12}$,
more preferably $R^3$ is:
  a) a cycloalkyl group,
  b) an aryl group, wherein the ring of the aryl group is unsubstituted or substituted with 1 to 5 substituents independently selected from the group consisting of a halogen atom, a lower alkyl group, a halo-lower alkyl group, a cyano group, a lower acyl group, a lower alkoxy group and a lower alkoxycarbonyl group, or
  c) a heteroaryl group, wherein the ring of the heteroaryl group is unsubstituted or substituted with 1 to 3 substituents independently selected from the group consisting of a halogen atom, a lower alkyl group, a halo-lower alkyl group and a lower alkoxy group; or $R^4$ is preferably:
a) a cyano group,
b) a lower alkoxycarbonyl group, or
c) a carboxy group.

In a preferable embodiment of the present invention, $R^1$ and $R^2$ are a hydrogen atom.

In a more preferable embodiment of the present invention, $R^1$ and $R^2$ are a hydrogen atom, and $R^3$ is:
a) a lower alkyl group,
b) a halo-lower alkyl group,
c) a cycloalkyl group,
d) a heterocycloalkyl group,
e) an aryl group, wherein the ring of the aryl group is unsubstituted or substituted with 1 to 5 substituents independently selected from the group consisting of a halogen atom, a lower alkyl group, a halo-lower alkyl group, a cyano group, a lower acyl group, a lower alkoxy group and a lower alkoxycarbonyl group,
f) a heteroaryl group, wherein the ring of the heteroaryl group is unsubstituted or substituted with 1 to 3 substituents independently selected from the group consisting of a halogen atom, a lower alkyl group, a halo-lower alkyl group and a lower alkoxy group,
g) an aralkyl group, wherein the ring of the aralkyl group is unsubstituted or substituted with 1 to 5 substituents independently selected from the group consisting of a halogen atom, a lower alkyl group, a halo-lower alkyl group and a lower alkoxy group,
h) a lower alkoxy group, or
i) —$NR^{11}R^{12}$.

In an even more preferable embodiment of the present invention, $R^1$ and $R^2$ are a hydrogen atom, $R^3$ is:
a) a lower alkyl group,
b) a halo-lower alkyl group,
c) a cycloalkyl group,
d) a heterocycloalkyl group,
e) an aryl group, wherein the ring of the aryl group is unsubstituted or substituted with 1 to 5 substituents independently selected from the group consisting of a halogen atom, a lower alkyl group, a halo-lower alkyl group, a cyano group, a lower acyl group, a lower alkoxy group and a lower alkoxycarbonyl group,
f) a heteroaryl group, wherein the ring of the heteroaryl group is unsubstituted or substituted with 1 to 3 substituents independently selected from the group consisting of a halogen atom, a lower alkyl group, a halo-lower alkyl group and a lower alkoxy group,
g) an aralkyl group, wherein the ring of the aralkyl group is unsubstituted or substituted with 1 to 5 substituents independently selected from the group consisting of a halogen atom, a lower alkyl group, a halo-lower alkyl group and a lower alkoxy group,
h) a lower alkoxy group, or
i) —$NR^{11}R^{12}$, and $R^4$ is:
a) a cyano group,
b) a lower alkoxycarbonyl group, or
c) a carboxy group.

In an especially preferable embodiment of the present invention,
$R^1$ and $R^2$ are a hydrogen atom,
$R^3$ is:
a) a cycloalkyl group,
b) an aryl group, wherein the ring of the aryl group is unsubstituted or substituted with 1 to 5 substituents independently selected from the group consisting of a halogen atom, a lower alkyl group, a halo-lower alkyl group, a cyano group, a lower acyl group, a lower alkoxy group and a lower alkoxycarbonyl group, or
c) a heteroaryl group, wherein the ring of the heteroaryl group is unsubstituted or substituted with 1 to 3 substituents independently selected from the group consisting of a halogen atom, a lower alkyl group, a halo-lower alkyl group and a lower alkoxy group, and $R^4$ is:
a) a cyano group,
b) a lower alkoxycarbonyl group, or
c) a carboxy group.

Specific examples of preferred embodiments of the present invention are compounds selected form the group consisting of:
ethyl 2-benzoyl-4,5-dihydroxy-3-nitrobenzoate;
methyl 2-benzoyl-4,5-dihydroxy-3-nitrobenzoate;
ethyl 4,5-dihydroxy-3-nitro-2-(thiophen-2-carbonyl)-benzoate;
4,5-dihydroxy-2-(4-methylbenzoyl)-3-nitrobenzonitrile
2-cyclohexanecarbonyl-4,5-dihydroxy-3-nitrobenzo-nitrile;
ethyl 4,5-dihydroxy-2-(isoxazole-5-carbonyl)-3-nitro-benzoate;
isopropyl 4,5-dihydroxy-2-(isoxazole-5-carbonyl)-3-nitrobenzoate;
ethyl 4,5-dihydroxy-3-nitro-2-(thiazole-2-carbonyl)-benzoate; and
4,5-dihydroxy-2-isobutyryl-3-nitrobenzonitrile.

Compound represented by general formula (I) can be prepared by the methods as illustrated in schemes 1 to 5.

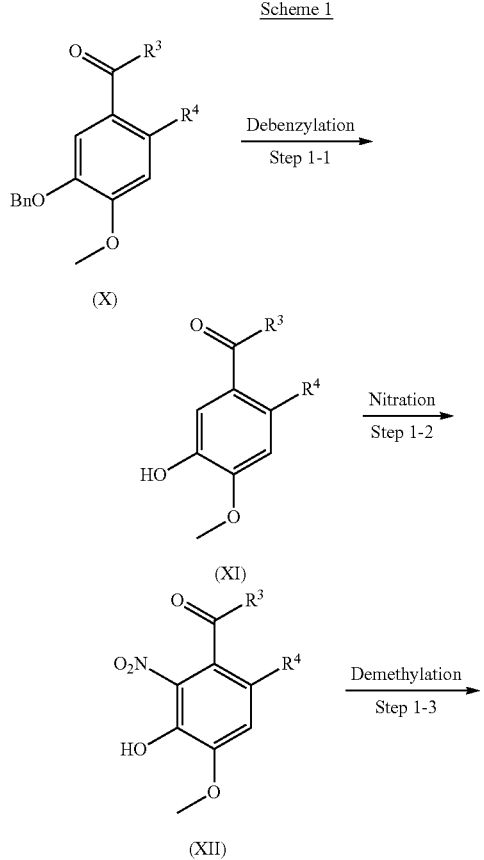

Scheme 1

-continued

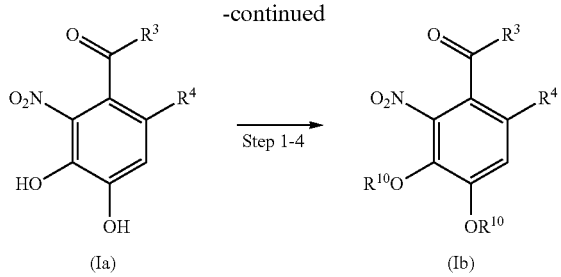

wherein $R^3$ and $R^4$ are as defined above, $R^{13}$ is a lower acyl or lower alkoxycarbonyl group or —CONR$^{11}R^{12}$, $R^{11}$ and $R^{12}$ are as defined above, and Bn is a benzyl group.

Step 1-1

The benzyl group of ketone derivative (X) is removed in the presence of a metal catalyst under an atomosphere of hydrogen in a suitable solvent to afford phenol derivative (XI). The solvents employed in the reaction include ethanol, N,N-dimethylformamide, tetrahydrofuran or the like. The metal catalysts include palladium carbon, platinum oxide or the like. The reaction is carried out ordinarily at room temperature to 80° C. The reaction time varies depending on the starting materials employed, the solvent, the reaction temperature or the like, but is usually 30 minutes to 12 hours.

Alternatively, the debenzylation reaction can be carried out by treating ketone derivative (X) with an acid or Lewis acid such hydrogen bromide, aluminum chloride, titanium tetrachloride or the like in an inert solvent such as methylene chloride, toluene or the like. The reaction is carried out ordinarily at 0° C. to 80° C. The reaction time varies depending on the starting materials employed, the solvent, the reaction temperature or the like, but is usually 15 minutes to 24 hours.

Step 1-2

Nitration of phenol derivative (XI) with a nitrating reagent in an inert solvent provides nitrophenol derivative (XII). The inert solvents employed in the reaction include methylene chloride, 1,2-dichloroethane, ethyl acetate, acetic acid, tetrahydrofuran or the like. The nitrating reagents include nitric acid, fuming nitric acid, nitronium tetrafluoroborate or the like. The reaction is carried out ordinarily at −40° C. to 80° C. The reaction time varies depending on the starting materials employed, the solvent, the reaction temperature or the like, but is usually 5 minutes to 12 hours. The nitration reaction can also be carried out, if desired, by adding an additive such as acetic anhydride, sulfuric acid or the like.

Step 1-3

Demethylation of nitrophenol derivative (XII) with a demethylation reagent in an inert solvent provides compound (Ia). The inert solvents employed in the reaction include ethyl acetate, pyridine, 1,4-dioxane or the like. The demethylation reagents include aluminum chloride-pyridine, boron tribromide or the like. The reaction is carried out ordinarily at −20° C. to 120° C. The reaction time varies depending on the starting materials employed, the solvent, the reaction temperature or the like, but is usually 1 hour to 24 hours.

Alternatively, the demethylation can be carried out by treating nitrophenol derivative (XII) with hydrobromic acid or hydroiodic acid in a solvent of acetic acid or without a solvent. The reaction is carried out ordinarily at 20° C. to reflux temperature. The reaction time varies depending on the starting materials employed, the solvent, the reaction temperature or the like, but is usually 1 hour to 24 hours.

Step 1-4

Acylation of compound (Ia) with an acylating reagent provides compound (Ib). Such acylation reactions are well known to those ordinarily skilled in the art, and can be carried out according to procedures as described in T. W. Green and P. G. H. Wuts, "Protective Groups in Organic Synthesis" the fourth edition.

Among compound (I) of the present invention, compound (Ic) and compound (Id) can be prepared by the methods as illustrated in scheme 2.

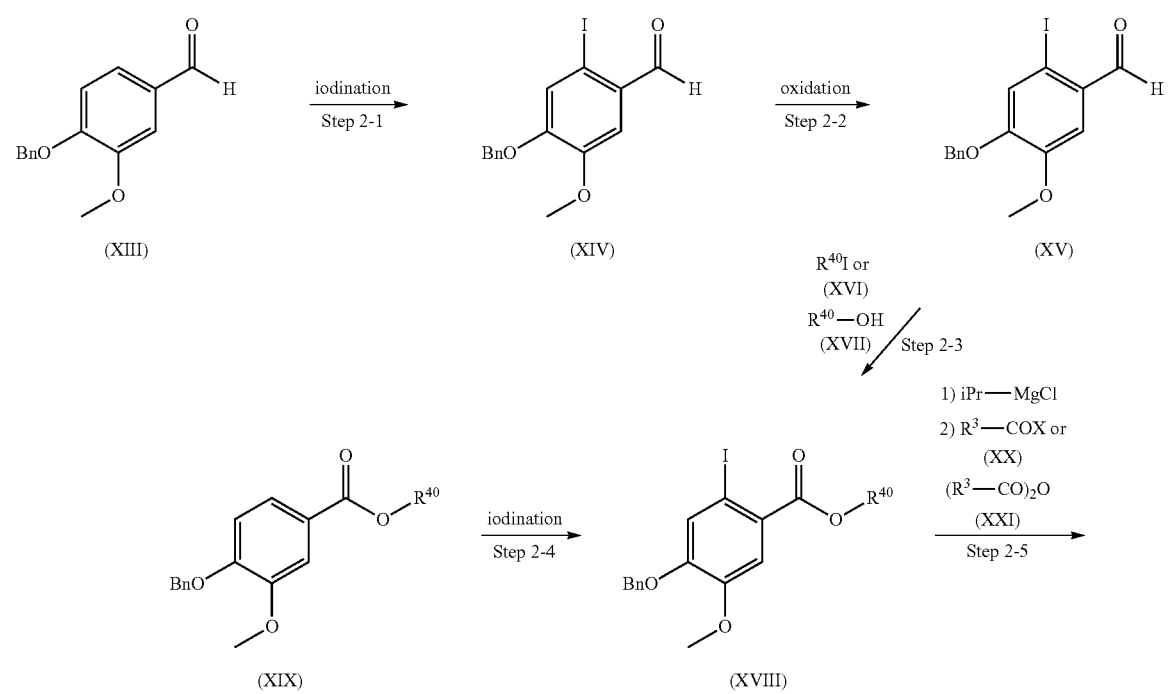

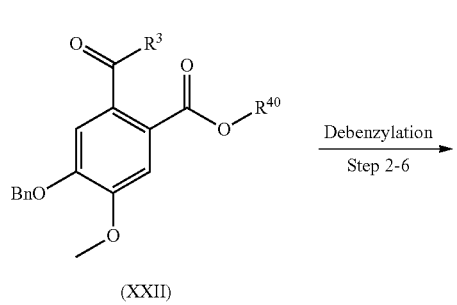
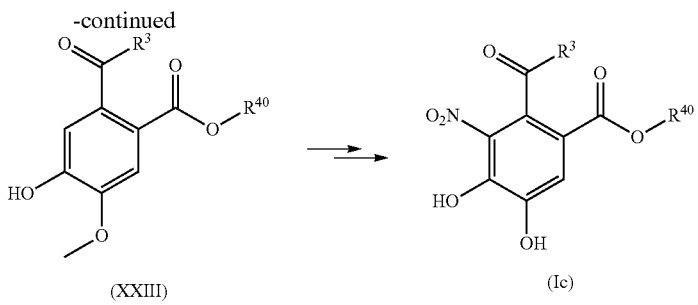
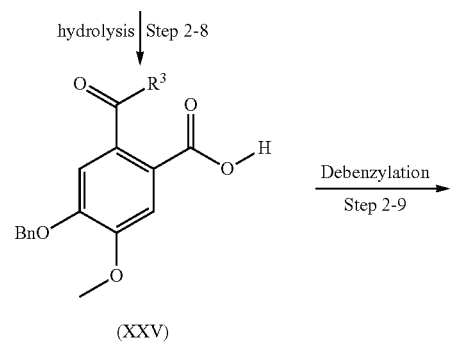
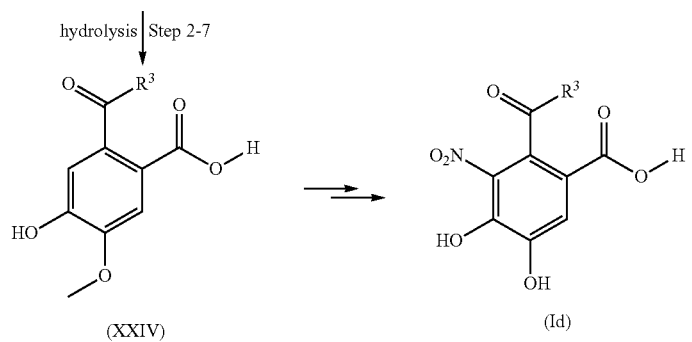

wherein $R^3$ and Bn are as defined above, $R^{40}$ is a lower alkyl, cycloalkyl, halo-lower alkyl, aryl or heteroaryl group, and X is a chloro or bromo atom.

Step 2-1

Iodination of aldehyde (XIII) with an iodinating reagent such as iodine, N-iodosuccinimide or iodine monochloride in a suitable solvent provides iodobenzaldehyde (XIV). The solvents employed in the reaction include methylene chloride, methanol, acetic acid or the like. The reaction is carried out ordinarily at 20° C. to reflux temperature. The reaction time varies depending on the starting materials employed, the reaction temperature or the like, but is usually 15 minutes to 24 hours. The iodination can be also carried out, if desired, by adding an additive such as trifluoroacetic acid, silver trifluoroacetate or the like.

Step 2-2

Oxidation of iodobenzaldehyde (XIV) with an oxidizing agent in a suitable solvent provides carboxylic acid (XV). The solvents employed in the reaction include methylene chloride, acetonitrile, water, methanol or the like. The oxidizing agents include potassium permanganate, manganese dioxide, sodium chlorite-hydrogen peroxide, sodium chlorite-dimethylsulfoxide or the like. The reaction is carried out ordinarily at 0° C. to 80° C. The reaction time varies depending on the starting materials employed, the solvent, the oxidizing agent, the reaction temperature or the like, but is usually 15 minutes to 3 days. The reaction can be carried out, if desired, by adding an additive such as sodium hydrogen phosphate, sulfuric acid or the like.

Step 2-3

Carboxylic acid (XV) is treated with alkyl iodide (XVI) in the presence of a base in an inert solvent to afford iodobenzoic acid ester derivative (XVIII). The inert solvents employed in the reaction include 1,4-dioxane, N, N-dimethylformamide, 1,2-dimethoxyethane, tetrahydrofuran or the like. The bases include sodium tert-butoxide, potassium tert-butoxide, potassium carbonate or the like. The reaction is carried out ordinarily at 0° C. to 100° C. The reaction time varies depending on the starting materials employed, the solvent, the reaction temperature or the like, but is usually 5 minutes to 24 hours.

The iodobenzoic acid ester derivative (XVIII) can be prepared by condensing carboxylic acid (XV) with alcohol (XVII) in the presence of a condensing agent in an inert solvent such as methylene chloride, N,N-dimethylformamide or the like. The condensing agents include dicyclohexylcarbodiimide, 1-(3-dimethylaminopropyl)-3-ethylcarbodiimide hydrochloride, diethyl cyanophosphate, diphenylphosphoryl-azide or the like. The reaction can be carried out, if desired, by adding a base such as triethylamine or the like.

Step 2-4

Iodination of ester derivative (XIX) with an iodinating reagent such as iodine, N-iodosuccinimide or iodine monochloride in a suitable solvent provides iodobonzoic acid ester (XVIII). The solvents employed in the reaction include methylene chloride, methanol, acetic acid or the like. The reaction is carried out ordinarily at 20° C. to reflux temperature. The reaction time varies depending on the starting materials employed, the reaction temperature or the like, but is usually 15 minutes to 24 hours. The iodination can be also carried out, if desired, by adding an additive such as trifluoroacetic acid, silver trifluoro-acetate or the like.

Step 2-5

Iodobenzoic acid ester derivative (XVIII) is treated with organic magnesium reagent in an inert solvent, followed by reaction with acid halide (XX) or acid anhydride (XXI) to afford ketone derivative (XXII). The inert solvents employed in the reaction include tetrahydrofuran or the like. The organic magnesium reagents include isopropylmagnesium chloride or the like. The reaction is carried out ordinarily at −78° C. to 50° C. The reaction time varies depending on the starting materials employed, the solvent, the reaction temperature or the like, but is usually 15 minutes to 2 hours.

Step 2-6

Debenzylation of ketone derivative (XXII) according to the procedures as described in Step 1-1 provides phenol derivative (XXIII).

Step 2-7

Hydrolysis of phenol derivative (XXIII) in the presence of a base in a suitable solvent provides carboxylic acid derivative (XXIV). The solvents employed in the reaction include methanol, ethanol, water, tetrahydrofuran, a mixed solvent thoreof or the like. The bases include sodium hydroxide, potassium hydroxide, lithium hydroxide or the like. The reaction is carried out ordinarily at room temperature to reflux temperature. The reaction time varies depending on the starting materials employed, the solvent, the reaction temperature or the like, but is usually 10 minutes to 24 hours.

Step 2-8

Hydrolysis of ketone derivative (XXII) according to the procedures as described in Step 2-7 provides carboxylic acid derivative (XXV).

Step 2-9

Debenzylation of carboxylic acid derivative (XXV) according to the procedures as described in Step 1-1 provides carboxylic acid derivative (XXIV).

Thereafter, compound (Ic) can be prepared from ester derivative (XXIII) according to the procedures as described in Step 1-2 to Step 1-3. Compound (Id) can be prepared from carboxylic acid (XXIV) according to the procedures as described in Step 1-2 to Step 1-3.

Among compound (I) of the present invention, compound (Ic) can be prepared by the methods as illustrated in scheme 3.

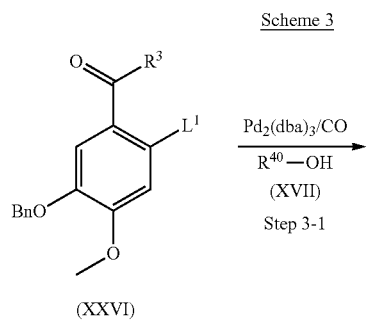

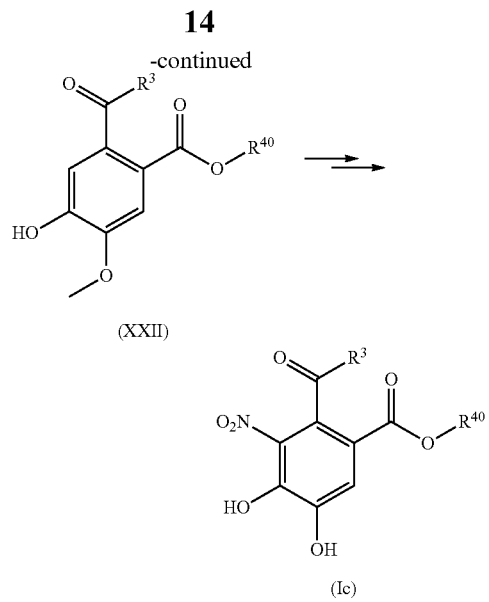

wherein $R^3$, $R^{40}$ and Bn are as defined above, $L^1$ is a bromine, iodine atom or a trifuluoromethanesulfonyloxy group.

Step 3-1

Condensation of compound (XXVI) with alcohol (XVII) under an atmosphere of carbon monoxide in the presence of a base, a palladium catalyst and a phosphine ligand in an inert solvent provides ester derivative (XXII). The inert solvents employed in the reaction include N,N-dimethylformamide, 1,4-dioxane, 1,2-dimethoxyethane, tetrahydrofuran, toluene or the like. The bases include triethylamine, N,N-diisopropylethylamine or the like. The palladium catalysts include tris(dibenzylidene-acetone)dipalladium(0), palladium acetate or the like. The phosphine ligands include 1,1'-bis(diphenylphosphino) ferrocene, triphenylphosphine or the like. The reaction is carried out ordinarily at 80° C. to 110° C. The reaction time varies depending on the starting materials employed, the solvent, the reaction temperature or the like, but is usually 1 hour to 24 hours.

Thereafter, compound (Ic) can be prepared from ester derivative (XXII) according to the procedures as described in Step 1-1 to Step 1-3.

Among compound (I) of the present invention, compound (Ie) can be prepared by the methods as illustrated in scheme 4.

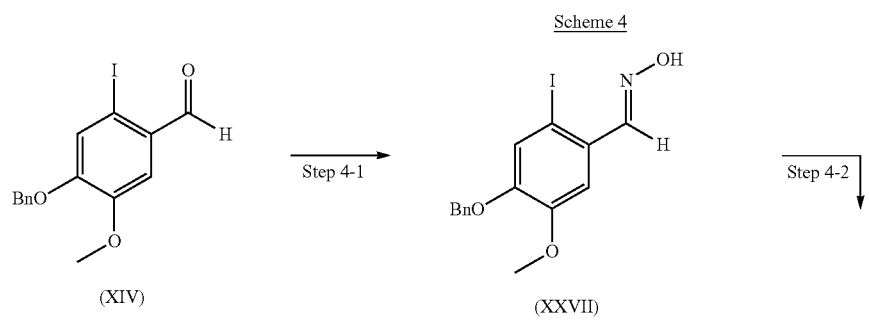

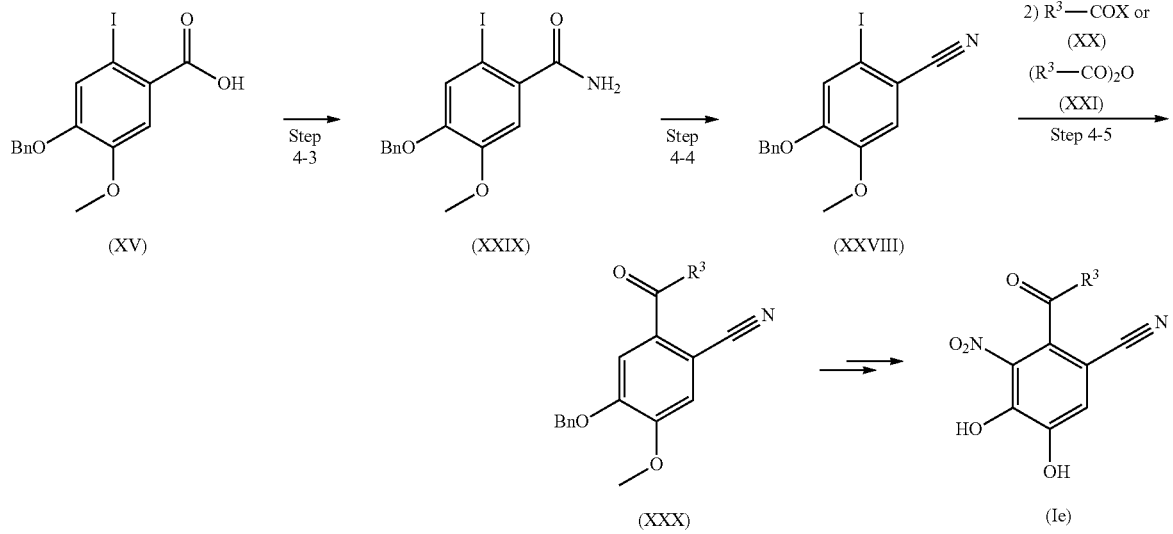

wherein $R^3$, Bn and X are as defined above.

Step 4-1

Oximation of iodobenzaldehyde (XIV) with hydroxylamine in a suitable solvent provides oxime (XXVII). The solvents employed in the reaction include ethanol, N, N-dimethylformamide, tetrahydrofuran or the like. The reaction is carried out ordinarily at 20° C. to reflux temperature. The reaction time varies depending on the starting materials employed, the reaction temperature or the like, but is usually 15 minutes to 24 hours. The oximation can also be carried out, if desired, by adding an additive such as sodium acetate or the like.

Step 4-2

Oxime (XXVII) is treated with acid anhydride, acid halide, sulfonic anhydride, sulfonyl chloride or thionyl chloride in the presence of a base in an inert solvent or using a base as a solvent to afford nitrile derivative (XXVIII). The solvents employed in the reaction include methylene chloride, tetrahydrofuran, ethyl acetate, toluene or the like. The bases include triethylamine, pyridine, N,N-dimethylaminopyridine or the like. Acid anhydrides include acetic anhydride, trifluoroacetic anhydride or the like. Acid halides include acetyl chloride, trifluoromethanesulfonyl chloride or the like. Sulfonic anhydrides include trifluoromethanesulfonic anhydride or the like. Sulfonyl chlorides include methanesulfonyl chloride, p-toluenesulfonyl chloride, trifluoromethanesulfonyl chloride or the like. The reaction is carried out ordinarily at −20° C. to 110° C. The reaction time varies depending on the starting materials employed, the solvent, the reaction temperature or the like, but is usually 30 minutes to 24 hours.

Step 4-3

Condensation of carboxylic acid (XV) with ammonia, aqueous ammonia or salts of ammonia in the presence of a condensing agent and a base such as triethylamine or the like in an inert solvent provides amide derivative (XXIX). The solvents employed in the reaction include acetonitrile, N,N-dimethylformamide, tetrahydrofuran, methylene chloride, a mixed solvent thereof or the like. The condensing agents include dicyclohexylcarbo-diimide, 1-(3-dimethylaminopropyl)-3-ethylcarbodiimide hydrochloride, diethyl cyanophosphate, diphenylphosphoryl-azide or the like.

Alternatively, amide derivative (XXIX) is obtained by converting carboxylic acid (XV) to its reactive derivatives such as acid halide, acid anhydride, benzotriazol-1-yl ester, 4-nitrophenyl ester, 2,5-dioxapyrrolidine ester or the like according to conventional methods, followed by the condensation with aqueous ammonia, ammonia or salts of ammonia in the presence or absence of a base. The solvents employed in the condensation reaction include acetonitrile, N,N-dimethylformamide, tetrahydrofuran, methylene chloride, a mixed solvent thereof or the like. The bases include potassium carbonate, triethylamine, N,N-diisopropylethylamine, pyridine, N-methylmorpholine, N,N-dimethylaniline or the like. The reaction is carried out ordinarily at −20° C. to reflux temperature. The reaction time varies depending on the starting materials employed, the solvent, the reaction temperature or the like, but is usually 15 minutes to 24 hours.

Step 4-4

Amide derivative (XXIX) is treated with acid anhydride, acid halide, sulfonic anhydride, sulfonyl chloride or thionyl chloride in the presence of a base in an inert solvent or using a base as a solvent to afford nitrile derivative (XXVIII). The solvents employed in the reaction include methylene chloride, tetrahydrofuran, ethyl acetate, toluene or the like. The bases include triethylamine, pyridine, N,N-dimethylaminopyridine or the like. Acid anhydrides include acetic anhydride, trifluoroacetic anhydride or the like. Acid halides include acetyl chloride, trifluoromethanesulfonyl chloride or the like. Sulfonic anhydrides include trifluoromethanesulfonic anhydride or the like. Sulfonyl chlorides include methanesulfonyl chloride, p-toluene sulfonyl chloride, trifluoromethane sulfonyl chloride or the like. The reaction is carried out ordinarily at −20° C. to 110° C. The reaction time varies depending on the starting materials employed, the solvent, the reaction temperature or the like, but is usually 30 minutes to 24 hours.

Step 4-5

Nitrile derivative (XXVIII) is treated with organic magnesium reagent in an inert solvent, followed by reaction with acid halide (XX) or acid anhydride (XXI) to afford ketone derivative (XXX). The inert solvents employed in the reaction include tetrahydrofuran or the like. The organic magnesium reagents include isopropylmagnesium chloride or the like.

The reaction is carried out ordinarily at −78° C. to 50° C. The reaction time varies depending on the starting materials employed, the solvent, the reaction temperature or the like, but is usually 15 minutes to 2 hours.

Therafter, compound (Ie) can be prepared from nitrile derivative (XXX) according to the procedures as described in Step 1-1 to Step 1-3.

Among compound (I) of the present invention, compound (Ie) can be prepared by the methods as illustrated in scheme 5.

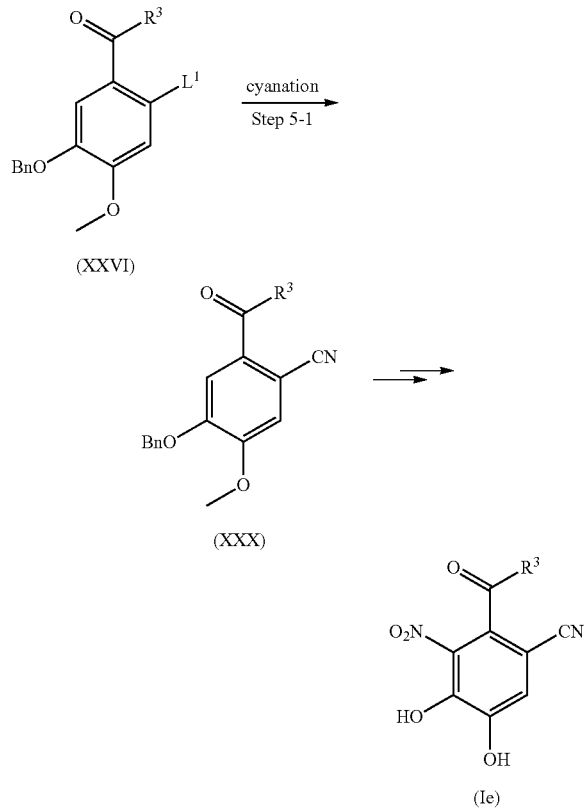

wherein $R^3$, Bn and $L^1$ are as defined above.

Step 5-1

Condensation of compound (XXVI) with a cyanating agent in the presence of a palladium catalyst and a ligand in an inert solvent provides nitrile derivative (XXX). The solvents employed in the reaction include 1,4-dioxane, N,N-dimethylformamide, 1,2-dimethoxyethane, 1-methyl-2-pyrrolidinone or the like. The cyanating agents include copper(I) cyanide, potassium cyanide or the like. The catalysts include tris(dibenzylidene-acetone)dipalladium(0) or the like. The ligands include 1,1'-bis(diphenylphosphino)ferrocene or the like. The reaction is carried out ordinarily at 80° C. to 110° C. The reaction time varies depending on the starting materials employed, the solvent, the reaction temperature or the like, but is usually 1 hour to 24 hours. The reaction can be carried out, if desired, by adding an additive such as tetraethylammonium cyanide or the like.

Thereafter, compound (Ie) can be prepared from nitrile derivative (XXX) according to the procedures as described in Step 1-1 to Step 1-3.

The forementioned schemes are exemplary for preparing compounds represented by general formula (I) of the present invention and synthetic intermediates thereof. Those ordinarily skilled in the art will appreciate that various changes or modifications of the forementioned schemes may be made without departing from the scope of the invention.

Compounds represented by general formula (I) of the present invention and intermediates for preparing the compounds of the present invention can be isolated or purified, if required, according to conventional isolation or purification techniques well known to those skilled in the art, such as solvent extraction, crystallization, recrystallization, chromatography, preparative high performance liquid chromatography or the like.

Compounds of general formula (I) exhibit excellent COMT inhibitory activities, and are useful as a therapeutic or prophylactic agent for Parkinson's disease. Compounds of general formula (I) are preferably used in combination with L-dopa. Compounds of general formula (I) may be used in combination with L-dopa and an aromatic L-amino acid decarboxylase inhibitor. Examples of aromatic L-amino acid decarboxylase inhibitors which may be used in combination with COMT inhibitors of the present invention, include carbidopa, benserazide or the like.

COMT inhibitors of the present invention can be used, if required, in combination with anti-Parkinson drugs other than L-dopa. Such anti-Parkinson drugs include droxidopa, melevodopa, threodops; dopamine $D_2$ receptor agonists such as cabergoline, bromocriptine mesylate, terguride, talipexole hydrochloride, ropinirole hydrochloride, pergolide mesylate, pramipexole hydrochloride, rotigotine and the like; anticholinergic agents such as profenamine, trihexyphenidyl hydrochloride, mazaticol hydrochloride, biperiden, piroheptinehydrochloride, methixene hydrochloride and the like; adenosine $A_{2A}$ receptor antagonists such as istradefylline and the like; NMDA antagonists such as budipine and the like; monoamine oxidase B inhibitors such as selegiline hydrochloride, rasagiline mesylate, safinamide mesylate and the like; zonisamide; amantadine hydrochloride and the like.

Compounds of the present invention are useful as a therapeutic or prophylactic agent for depression. Compounds of the present invention are useful as a therapeutic agent for hypertension since compounds of the present invention exhibit urinary sodium excretion promoting activities.

Pharmaceutical compositions comprising a compound of general formula (I) or a pharmaceutically acceptable salt thereof can be administered in various dosage forms depending on their usages. Exemplary dosage forms include powders, granules, fine granules, dry syrups, tablets, capsules, injections, liquids, ointments, suppositories, poultices and the like, which are administered orally or parenterally.

Pharmaceutical compositions can be formulated by admixing, diluting or dissolving with appropriate pharmaceutical carriers such as excipients, disintegrators, binders, lubricants, diluents, buffers, isotonic agents, preservatives, wetting agents, emulsifying agents, dispersing agents, stabilizing agents, solubilizing agents and the like, according to a conventional formulation procedure depending upon their dosage forms.

The dosage of a compound represented by general formula (I) or a pharmaceutically acceptable salt thereof is appropriately determined depending on the age, sex or body weight of the individual patient, the severity of the disease, the condition to be treated and the like. A typical dosage for oral administration is in the range of from about 10 mg to about 3000 mg per day per adult human. A typical dosage for parenteral administration is in the range of from about 5 mg to about 1000 mg per day per adult human. The dosages may be administered in single or divided doses, for example one to several times daily.

A pharmaceutical combination comprising a compound represented by general formula (I) or a pharmaceutically acceptable salt thereof, and at least one selected from L-dopa and an aromatic L-amino acid decarboxylase inhibitor, can be administered as a single pharmaceutical composition comprising all of active ingredients, or as separately formulated pharmaceutical compositions each of which comprises a single active ingredient. Where separately formulated pharmaceutical compositions are used, the compositions may be administered separately, concurrently or at different intervals. Alternatively, where separately formulated pharmaceutical compositions are used, the compositions may be mixed together with an appropriate diluent, and administered simultaneously.

In a pharmaceutical combination comprising a compound represented by general formula (I) or a pharmaceutically acceptable salt thereof, and at least one selected from L-dopa and an aromatic L-amino acid decarboxylase inhibitor, the dosage of each active ingredient may be appropriately determined depending on the age, sex or body weight of the individual patient, the severity of the disease, administration time, dosage form, administration method, combination of active ingredients and the like.

The following reference examples, examples and test examples illustrate the invention in further detail. It is to be understood, however, that they are not to be construed as limiting the scope of the invention in any way.

EXAMPLE

Reference Example 1-1

4-Benzyloxy-2-iodo-5-methoxybenzaldehyde

To a mixture of 4-benzyloxy-3-methoxybenzaldehyde (10 g), silver trifluoroacetate (11.4 g) and methylene chloride (105 mL) was added iodine (13.1 g) at room temperature. After stirring for 2 hours, the mixture was passed through a layer of Celite (registered mark). The filtrate was washed with an aqueous solution of sodium hydrogen sulfite and brine successively, dried over anhydrous magnesium sulfate, and concentrated under reduced pressure. The residue was triturated with methanol: water=4:1 to give the title compound (13.2 g).

$^1$H-NMR (CDCl$_3$) δ ppm: 3.91 (3H, s), 5.19 (2H, s), 7.30-7.50 (7H, m), 9.86 (1H, s)

Reference examples 1-2 to 1-3 were prepared in a manner similar to those as described in reference example 1-1 using the corresponding dioxybenzenes instead of 4-benzyloxy-3-methoxybenzaldehyde. These were illustrated in table 1.

TABLE 1

| Reference example | Structure |
| --- | --- |
| 1-1 | (structure) |

TABLE 1-continued

| Reference example | Structure |
| --- | --- |
| 1-2 | (structure) |
| 1-3 | (structure) |

The physical data of reference examples 1-2 to 1-3 were shown below.

Reference Example 1-2

$^1$H-NMR (CDCl$_3$) δ ppm: 3.95 (3H, s), 5.16 (2H, s), 7.29-7.47 (6H, m), 7.48 (1H, s), 9.84 (1H, s)

Reference Example 1-3

$^1$H-NMR (CDCl$_3$) δ ppm: 3.89 (3H, s), 3.91 (3H, s), 5.15 (2H, s), 7.30-7.50 (7H, m)

Reference Example 2-1

4-Benzyloxy-2-iodo-5-methoxybenzaldehyde oxime

A mixture of 4-benzyloxy-2-iodo-5-methoxybenzaldehyde (reference example 1-1) (12.2 g), hydroxylamine hydrochloride (2.54 g), sodium acetate (6 g) and ethanol (170 mL) was stirred at 70° C. for 1.5 hours. The mixture was concentrated under reduced pressure. Water was added to the residue, and the mixture was stirred at room temperature for 30 minutes. The solid was collected by filtration to give the title compound (12.8 g).

$^1$H-NMR (CDCl$_3$) δ ppm: 3.88 (3H, s), 5.13 (2H, s), 7.19 (1H, s), 7.29 (1H, s), 7.30-7.50 (6H, m), 8.30 (1H, s)

Reference Example 3-1

4-Benzyloxy-2-iodo-5-methoxybenzonitrile

To a mixture of 4-benzyloxy-2-iodo-5-methoxybenzaldehyde oxime (reference example 2-1) (20.8 g), triethylamine (22.7 mL) and tetrahydrofuran (181 mL) was added trifluoroacetic anhydride (23 mL) under ice-bath cooling. After stirring at room temperature for an hour, 2 mol/L hydrochloric acid and ethyl acetate were added to the mixture. The organic layer was washed with brine, and dried over anhydrous magnesium sulfate, and concentrated under reduced pressure. The residue was triturated with methanol to give the title compound (10.25 g).

$^1$H-NMR (CDCl$_3$) δ ppm: 3.87 (3H, s), 5.15 (2H, s), 7.05 (1H, s), 7.31 (1H, s), 7.30-7.42 (5H, m)

Reference example 3-1 can also be prepared in a manner as described in reference example 4-1.

Reference Example 4-1

4-Benzyloxy-2-iodo-5-methoxybenzonitrile

To a mixture of 4-benzyloxy-2-iodo-5-methoxybenzamide (reference example 6-3) (5.25 g) and dichloromethane (70 mL) were added triethylamine (8.2 mL) and trifluoromethanesulfonic anhydride (4.6 mL) at 0° C. The mixture was stirred at 0° C. for 20 minutes, at room temperature for 3.5 hours and at reflux temperature for an hour. After cooling to 0° C., to the mixture were added triethylamine (4 mL) and trifluoromethanesulfonic anhydride (2.3 mL). After stirring at room temperature overnight, to the mixture were added ice-water and 1 mol/L hydrochloric acid. The mixture was extracted with ethyl acetate. The organic layer was washed with 1 mol/L hydrochloric acid and brine successively, dried over anhydrous magnesium sulfate, and concentrated under reduced pressure. A mixture of the residue, ethyl acetate, dichloromethane, silicagel and aminopropylsilicagel was stirred for 30 minutes. The mixture was passed through a layer of Celite (registered mark). The filtrate was concentrated under reduced pressure. The residue was triturated with methanol to give the title compound (3.72 g).

Reference Example 5-1

4-Benzyloxy-2-iodo-5-methoxybenzoic acid

A mixture of 4-benzyloxy-2-iodo-5-methoxybenzaldehyde (reference example 1-1) (20 g), dimethylsulfoxide (19 mL), concentrated sulfuric acid (3 mL), water (30 mL) and acetonitrile (181 mL) was added a mixture of sodium chlorite (9.8 g) and water (30 mL). After stirring at room temperature for 30 minutes, water was added to the mixture. Insoluble materials were collected by filtration to give the title compound (20.3 g).

$^1$H-NMR (CDCl$_3$) δ ppm: 3.88 (3H, s), 5.15 (2H, s), 7.31-7.46 (6H, m), 7.56 (1H, s)

Reference examples 5-2 to 5-3 were prepared in a manner similar to those as described in reference example 5-1 using the corresponding benzaldehydes instead of 4-benzyloxy-2-iodo-5-methoxybenzaldehyde. These were illustrated in table 2.

TABLE 2

| Reference example | Structure |
|---|---|
| 5-1 | (structure) |
| 5-2 | (structure) |
| 5-3 | (structure) |

The physical data of reference example 5-2 to examples 5-3 were shown below.

Reference Example 5-2

$^1$H-NMR (DMSO-d$_6$) δ ppm: 3.84 (3H, s), 5.11 (2H, s), 7.30-7.50 (6H, m), 7.56 (1H, s), 13.00 (1H, br)

Reference Example 5-3

$^1$H-NMR (DMSO-d$_6$) δ ppm: 3.91 (3H, s), 5.25 (2H, s), 7.33-7.47 (5H, m), 7.51 (1H, s), 7.67 (1H, s), 13.59 (1H, br s)

Reference Example 6-1

(5-Benzyloxy-2-iodo-4-methoxyphenyl)piperidin-1-yl-methanone

To a mixture of 5-benzyloxy-2-iodo-4-methoxybenzoic acid (reference example 5-2) (1.92 g), piperidine (0.74 mL) and N,N-dimethylforamide (12 mL) was added 1-hydroxybenzotriazole (676 mg) and 1-ethyl-3-(3-dimethylaminopropyl)carbodiimide hydrochloride (1.44 g) at room temperature. The mixture was stirred at room temperature for 6 hours. After addition of ethyl acetate, the mixture was poured into 2 mol/L hydrochloric acid. The organic layer was washed with water, an aqueous solution of sodium bicarbonate, and brine successively, dried over anhydrous magnesium sulfate, and concentrated under reduced pressure. The mixture of the residue, aminopropylsilicagel and dichloromethane was stirred for 30 minutes. Insoluble materials were removed by filtration. The filtrate was concentrated under reduced pressure to give the title compound (2.13 g).

$^1$H-NMR (CDCl$_3$) δ ppm: 1.21-1.71 (6H, m), 2.97-3.14 (2H, m), 3.56-3.81 (2H, m), 3.88 (3H, s), 5.05-5.18 (2H, m), 6.70 (1H, s), 7.22 (1H, s), 7.27-7.40 (5H, m)

Reference examples 6-2 to 6-9 were prepared in a manner similar to those as described in Reference example 6-1 using the corresponding carboxylic acids and amines instead of 5-benzyloxy-2-iodo-4-methoxybenzoic acid and piperidine. These were illustrated in table 3.

TABLE 3
| Reference example | Structure |
|---|---|
| 6-1 | 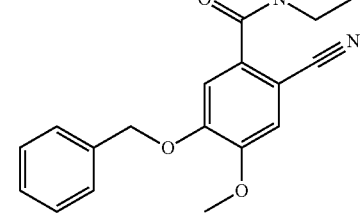 |
| 6-2 | 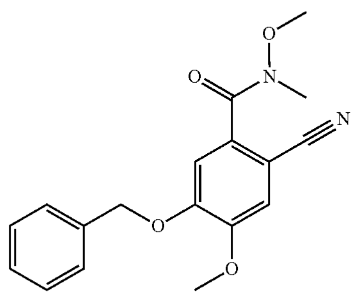 |
| 6-3 | 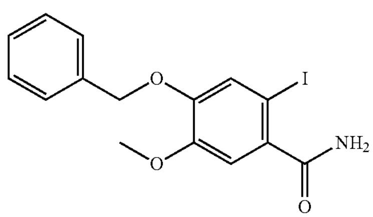 |
| 6-4 | 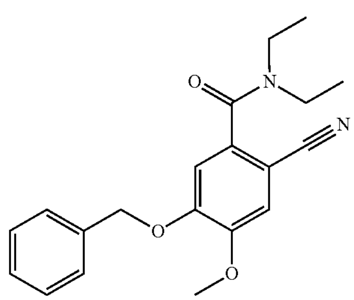 |
| 6-5 | 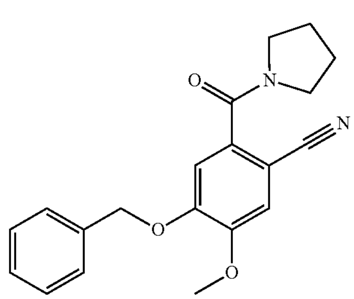 |
| 6-6 | 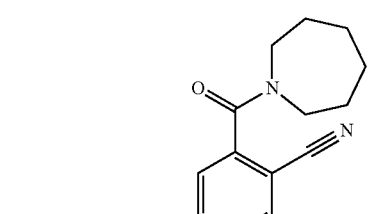 |
| 6-7 | |
| 6-8 | |
| 6-9 | |
The physical data of reference example 6-2 to examples 6-9 were shown below.
Reference Example 6-2
$^1$H-NMR (CDCl$_3$) δ ppm: 3.34 (3H, s), 3.42 (3H, brs), 3.94 (3H, s), 5.22 (2H, s), 7.08 (1H, s), 7.12 (1H, s), 7.25-7.45 (5H, m)
Reference Example 6-3
$^1$H-NMR (CDCl$_3$) δ ppm: 3.88 (3H, s), 5.13 (2H, s), 5.50-6.20 (2H, m), 7.13 (1H, s), 7.25-7.50 (6H, m)

Reference Example 6-4

$^1$H-NMR (CDCl$_3$) δ ppm: 0.93 (3H, m), 1.27 (3H, m), 3.04-3.20 (2H, m), 3.48-3.61 (2H, m), 3.92 (3H, s), 5.21 (2H, s), 6.86 (1H,$), 7.09 (1H, s), 7.30-7.41 (5H, m)

Reference Example 6-5

$^1$H-NMR (CDCl$_3$) δ ppm: 1.82-1.89 (2H, m), 1.93-2.00 (2H, m), 3.18 (2H, t, J=6.7 Hz), 3.65 (2H, t, J=7.0 Hz), 3.92 (3H, s), 5.20 (2H, s), 6.96 (1H, s), 7.10 (1H, s), 7.31-7.42 (5H, m)

Reference Example 6-6

$^1$H-NMR (CDCl$_3$) δ ppm: 1.38-1.53 (2H, m), 1.60-1.75 (4H, m), 3.09-3.27 (2H, m), 3.62-3.79 (2H, m), 3.92 (3H, s), 5.19 (2H, s), 6.91 (1H, s), 7.09 (1H, s), 7.31-7.42 (5H, m)

Reference Example 6-7

$^1$H-NMR (CDCl$_3$) δ ppm: 1.40-1.64 (6H, m), 1.80-1.86 (2H, m), 3.18 (2H, t, J=6.0 Hz), 3.67 (2H, t, J=5.9 Hz), 3.92 (3H, s), 5.21 (2H, s), 6.84 (1H, s), 7.09 (1H, s), 7.30-7.40 (5H, m)

Reference Example 6-8

$^1$H-NMR (CDCl$_3$) δ ppm: 3.22 (2H, m), 3.58 (2H, m), 3.78 (4H, m), 3.93 (3H, s), 5.21 (2H, s), 6.91 (1H, s), 7.10 (1H, s), 7.31-7.40 (5H, m)

Reference Example 6-9

$^1$H-NMR (CDCl$_3$) δ ppm: 1.28 (3H, t, J=7.0 Hz), 3.14-3.84 (8H, m), 3.93 (3H, s), 4.17 (2H, q, J=7.0 Hz), 5.21 (2H, s), 6.91 (1H, s), 7.11 (1H, s), 7.32-7.40 (5H, m)

Reference Example 7-1

Ethyl 4-benzyloxy-2-iodo-5-methoxybenzoate

A mixture of 4-benzyloxy-2-iodo-5-methoxybenzoic acid (reference example 5-1) (2 g), 2-iodoethane (0.5 mL), potassium carbonate (1.08 g) and N,N-dimethylformamide (17 mL) was stirred at room temperature for 2 hours. Water was added to the mixture. Insoluble materials were collected by filtration to give the title compound (2.07 g).
$^1$H-NMR (CDCl$_3$) δ ppm: 1.41 (3H, t, J=7.1 Hz), 3.89 (3H, s), 4.38 (2H, q, J=7.1 Hz), 5.15 (2H, s), 7.30-7.46 (7H, m)

Reference Example 7-2

Isopropyl 4-benzyloxy-2-iodo-5-methoxybenzoate

Title compound was prepared in a manner similar to those as described in reference example 7-1 using 2-iodopropane instead of 2-iodoethane.
$^1$H-NMR (CDCl$_3$) δ ppm: 1.39 (6H, d, J=6.3 Hz), 3.89 (3H, s), 5.15 (2H, s), 5.21-5.29 (1H, m), 7.30-7.45 (7H, m)

Reference Example 8-1

Isopropyl 4-benzyloxy-5-methoxy-2-(piperidine-1-carbonyl)-benzoate

A mixture of tris(dibenzylideneacetone)dipalladium(0) (157 mg), 1,1'-bis(diphenylphosphino)ferrocene (380 mg) and N,N-dimethylformamide (10 mL) was stirred under an argon atmosphere for 10 minutes. To the mixture were added (5-benzyloxy-2-iodo-4-methoxyphenyl)piperidin-1-yl-methanone (reference example 6-1) (1.55 g), 2-propanol (10 mL) and triethylamine (1.44 mL). After displacement to a carbon monoxide atmosphere, the mixture was stirred at 90° C. for 14 hours. After cooling to room temperature, to the mixture were added ethyl acetate and 2 mol/L hydrochloric acid. The separated organic layer was washed with water, a 2 mol/L aqueous solution of sodium hydroxide, an aqueous solution of sodium bicarbonate and brine successively, dried over anhydrous magnesium sulfate, and concentrated under reduced pressure. The residue was purified by silica gel column chromatography (eluent: 15%-45% ethyl acetate/hexane, gradient elution) to give the title compound (258 mg).
$^1$H-NMR (CDCl$_3$) δ ppm: 1.10-1.80 (12H, m), 2.82-3.30 (3H, m), 3.94 (3H, s), 4.05-4.20 (1H, m), 5.10-5.30 (3H, m), 6.71 (1H, s), 7.28-7.42 (5H, m), 7.52 (1H, s)

Reference Example 8-2

Ethyl 4-benzyloxy-5-methoxy-2-(piperidine-1-carbonyl)-benzoate

The title compound was prepared in a manner similar to those as described in reference example 8-1 using ethanol instead of isopropanol.
$^1$H-NMR (CDCl$_3$) δ ppm: 1.10-1.75 (9H, m), 2.91-3.50 (3H, m), 3.91-4.05 (4H, m), 4.31 (2H, q, J=7.0 Hz), 5.20 (2H, brs), 6.72 (1H, s), 7.28-7.45 (5H, m), 7.53 (1H, s)

Reference Example 9-1

(5-Benzyloxy-2-bromo-4-methoxyphenyl)p-tolyl-methanol

To a mixture of 5-benzyloxy-2-bromo-4-methoxy-benzaldehyde (1 g) and tetrahydrofuran (10 mL) was added p-tolyl-magnesium bromide (1 mol/L tetrahydrofuran solution, 3.7 mL) under ice-salt bath cooling. After stirring at same temperature for 10 minutes, to the mixture were added an aqueous solution of ammonium chloride, ethyl acetate and 2 mol/L hydrochloric acid. The separated organic layer was dried over anhydrous magnesium sulfate, and concentrated under reduced pressure. The residue was purified by silica gel column chromatography (eluent: 0%-50% ethyl acetate/hexane, gradient elution) to give the title compound (1.27 g).
$^1$H-NMR (CDCl$_3$) δ ppm: 2.32 (3H, s), 3.85 (3H, s), 5.04-5.20 (2H, m), 6.03 (1H, d, J=3.3 Hz), 6.99 (1H, s), 7.06-7.17 (5H, m), 7.27-7.39 (5H, m)

Reference Example 9-2

(5-Benzyloxy-2-bromo-4-methoxyphenyl)cyclohexylmethanol

The title compound was prepared in a manner similar to those as described in reference example 9-1 using cyclohexylmagnesium bromide instead of p-tolylmagnesium bromide.
$^1$H-NMR (CDCl$_3$) δ ppm: 0.95-1.18 (5H, m), 1.29-1.36 (1H, m), 1.46-1.81 (7H, m), 3.86 (3H, s), 4.70-4.76 (1H, m), 5.10-5.23 (2H, m), 6.98 (1H, s), 7.27-7.45 (5H, m)

Reference Example 10-1

(5-Benzyloxy-2-bromo-4-methoxyphenyl)p-tolyl-methanone

A mixture of 5-benzyloxy-2-bromo-4-methoxyphenyl)-p-tolylmethanol (reference example 9-1) (1.27 g), manganese dioxide (2.67 g) and dichloromethane (30 mL) was stirred at room temperature overnight. Insoluble materials were removed by celite (registered mark) filtration. The filtrate was concentrated under reduced pressure to give the title compound (1.11 g).

$^1$H-NMR (CDCl$_3$) δ ppm: 2.42 (3H, s), 3.94 (3H, s), 5.09 (2H, s), 6.91 (1H, s), 7.10 (1H, s), 7.22 (2H, d, J=7.8 Hz), 7.29-7.40 (5H, m), 7.64 (2H, d, J=8.3 Hz)

Reference Example 10-2

(5-Benzyloxy-2-bromo-4-methoxyphenyl)cyclohexylmethanone

A mixture of (5-benzyloxy-2-bromo-4-methoxyphenyl)-cyclohexylmethanol (Reference example 9-2) (580 mg), triethylamine (0.797 mL) and dimethylsulfoxide (21 mL) was added pyridine sulfur trioxide complex (684 mg) under ice-bath cooling. After stirring at room temperature for an hour, water and ethyl acetate were added to the mixture. The organic layer was washed with water, dried over anhydrous magnesium sulfate, and concentrated under reduced pressure. The residue was purified by silica gel column chromatography (eluent: 0%-50% ethyl acetate/hexane, gradient elution) to give the title compound (348 mg).

$^1$H-NMR (CDCl$_3$) δ ppm: 1.14-1.44 (5H, m), 1.59-1.87 (5H, m), 2.92-3.05 (1H, m), 3.89 (3H, s), 5.13 (2H, s), 6.88 (1H,$), 7.04 (1H, s), 7.23-7.44 (5H, m)

Reference Example 11-1

Ethyl 2-benzoyl-4-benzyloxy-5-methoxybenzoate

To a mixture of ethyl 4-benzyloxy-2-iodo-5-methoxy-benzoate (reference example 7-1) (1 g) and tetrahydrofuran (25 mL) was added isopropylmagnesium chloride (2.0 mol/L tetrahydro-furan solution, 1.58 mL) under an argon atmosphere at −78° C. After stirring at −78° C. for 10 minutes, benzoic anhydride (1.1 g) was added to the mixture. After stirring at −78° C. for 30 minutes and at room temperature for 30 minutes, water, 2 mol/L hydrochloric acid and ethyl acetate were added to the mixture. The separated organic layer was washed with brine, dried over anhydrous magnesium sulfate, and concentrated under reduced pressure. The residue was purified by silica gel column chromatography (eluent: 0%-50% ethyl acetate/hexane, gradient elution) to give the title compound (848 mg).

$^1$H-NMR (CDCl$_3$) δ ppm: 0.98 (3H, t, J=7.2 Hz), 3.93-4.05 (6H, m), 5.18 (2H, s), 6.93 (1H, s), 7.28-7.66 (11H, m)

Reference examples 11-2 to 11-31 were prepared in a manner similar to those as described in Reference example 11-1 using the corresponding iodobenzenes and acid anhydrides or acid chlorides instead of ethyl 4-benzyloxy-2-iodo-5-methoxy-benzoate and benzoic anhydride. These were illustrated in table 4.

TABLE 4

| Reference example | Structure |
|---|---|
| 11-1 | (structure) |
| 11-2 | (structure) |
| 11-3 | (structure) |
| 11-4 | (structure) |
| 11-5 | (structure) |

TABLE 4-continued

| Reference example | Structure |
|---|---|
| 11-6 | |
| 11-7 | |
| 11-8 | |
| 11-9 | |
| 11-10 | 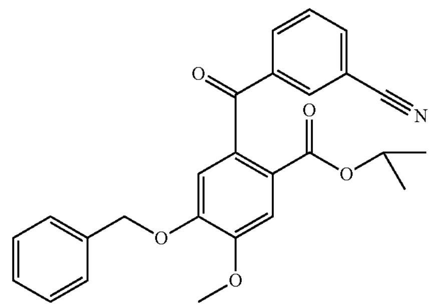 |
| 11-11 | 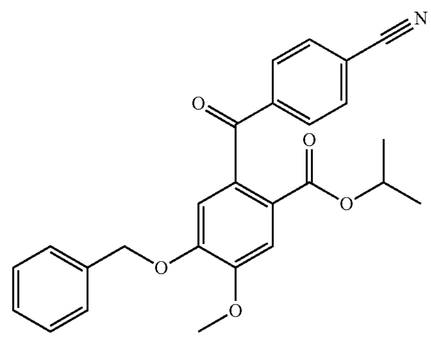 |
| 11-12 | 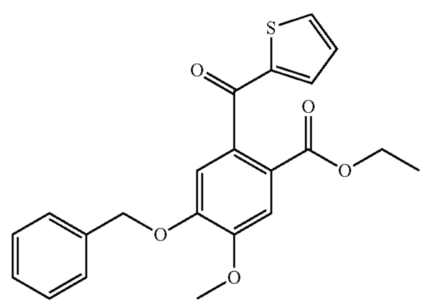 |
| 11-13 | 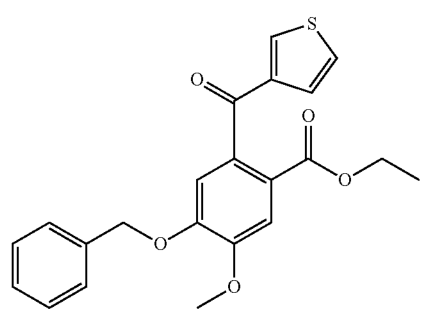 |
| 11-14 | 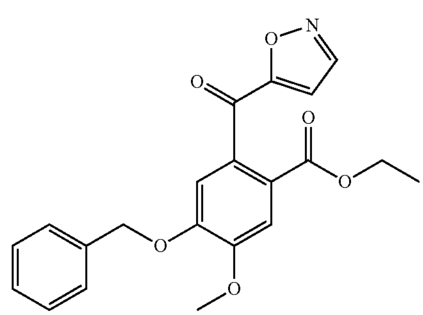 |

TABLE 4-continued

| Reference example | Structure |
|---|---|
| 11-15 | 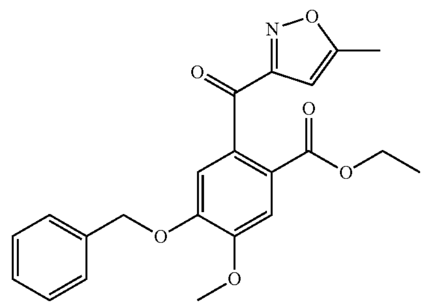 |
| 11-16 | 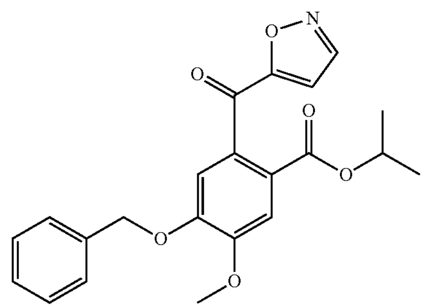 |
| 11-17 | 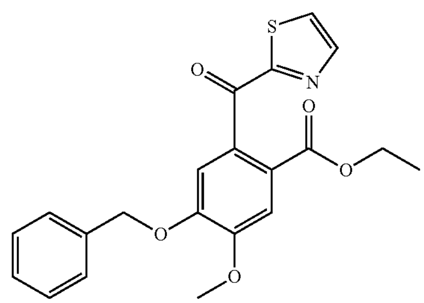 |
| 11-18 | 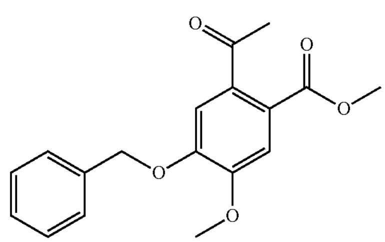 |
| 11-19 | 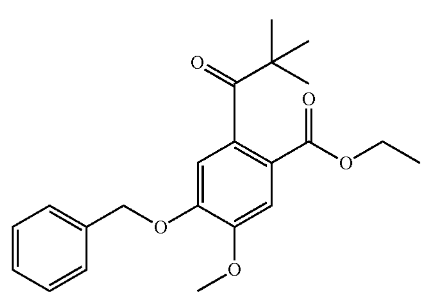 |
| 11-20 | |
| 11-21 | |
| 11-22 | |
| 11-23 | |
| 11-24 | |

TABLE 4-continued

| Reference example | Structure |
|---|---|
| 11-25 | 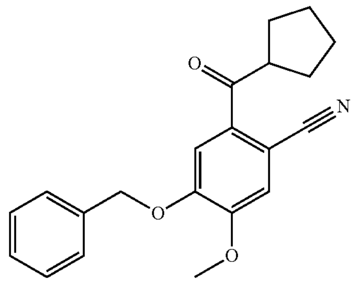 |
| 11-26 | 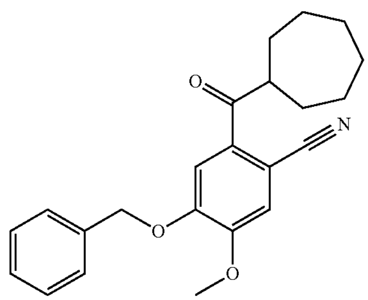 |
| 11-27 | 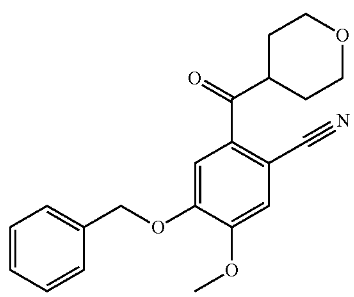 |
| 11-28 | 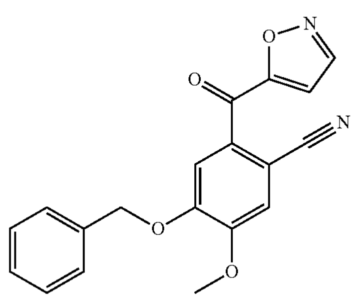 |
| 11-29 | 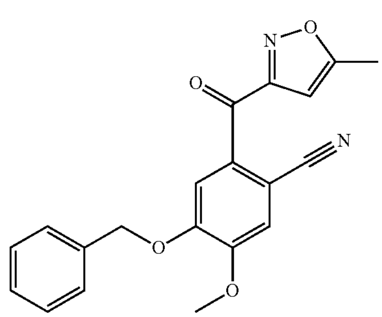 |
| 11-30 | 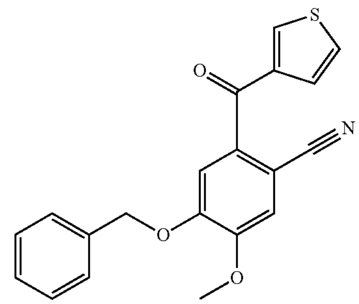 |
| 11-31 | 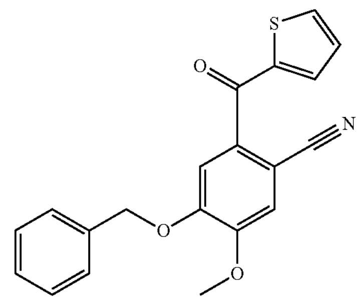 |

The physical data of reference example 11-2 to examples 11-31 were shown below.

Reference Example 11-2

$^1$H-NMR (CDCl$_3$) δ ppm: 3.52 (3H, s), 3.99 (3H, s), 5.17 (2H, s), 6.95 (1H, s), 7.27-7.65 (11H, m)

Reference Example 11-3

$^1$H-NMR (CDCl$_3$) δ ppm: 0.95 (6H, d, J=6.3 Hz), 3.99 (3H, s), 4.85-4.97 (1H, m), 5.16 (2H, s), 6.89 (1H, s), 7.29-7.44 (7H, m), 7.49-7.59 (2H, m), 7.69-7.76 (2H, m)

Reference Example 11-4

$^1$H-NMR (CDCl$_3$) δ ppm: 1.09 (3H, t, J=7.2 Hz), 3.98 (3H, s), 4.07 (2H, q, J=7.2 Hz), 5.17 (2H, s), 6.94 (1H, s), 7.00-7.15 (1H, m), 7.15-7.25 (1H, m), 7.25-7.45 (5H, m), 7.45-7.60 (2H, m), 7.60-7.75 (1H, m)

Reference Example 11-5

$^1$H-NMR (CDCl$_3$) δ ppm: 1.04 (3H, t, J=7.2 Hz), 3.95-4.10 (5H, m), 5.18 (2H, s), 6.89 (1H, s), 7.15-7.50 (9H, m), 7.55 (1H, s)

Reference Example 11-6

$^1$H-NMR (CDCl$_3$) δ ppm: 1.00 (3H, t, J=7.2 Hz), 2.40 (3H, s), 3.95-4.10 (5H, m), 5.16 (2H, s), 6.91 (1H, s), 7.15-7.25 (2H, m), 7.25-7.45 (5H, m), 7.54 (1H, s), 7.55-7.65 (2H, m)

Reference Example 11-7

$^1$H-NMR (CDCl$_3$) δ ppm: 1.01 (6H, d, J=6.3 Hz), 3.99 (3H, s), 4.89-5.01 (1H, m), 5.16 (2H, s), 6.85 (1H, s), 7.28-7.43 (5H, m), 7.50-7.61 (5H, m)

Reference Example 11-8

¹H-NMR (CDCl₃) δ ppm: 0.96 (6H, d, J=6.3 Hz), 3.95 (3H, s), 4.01 (3H, s), 4.85-5.00 (1H, m), 5.17 (2H, s), 6.88 (1H, s), 7.20-7.50 (5H, m), 7.57 (1H, s), 7.70-7.85 (2H, m), 8.00-8.15 (2H, m)

Reference Example 11-9

¹H-NMR (CDCl₃) δ ppm: 1.13 (6H, d, J=6.3 Hz), 3.99 (3H, s), 4.95-5.10 (1H, m), 5.13 (2H, s), 6.92 (1H, s), 7.20-7.45 (9H, m), 7.55-7.70 (1H, m)

Reference Example 11-10

¹H-NMR (CDCl₃) δ ppm: 1.04 (6H, d, J=6.3 Hz), 4.02 (3H, s), 4.89-5.01 (1H, m), 5.19 (2H, s), 6.84 (1H, s), 7.30-7.42 (5H, m), 7.51-7.58 (2H, m), 7.78-7.83 (1H, m), 7.90-7.93 (1H, m), 7.95-8.00 (1H, m)

Reference Example 11-11

¹H-NMR (CDCl₃) δ ppm: 1.02 (6H, d, J=6.3 Hz), 4.00 (3H, s), 4.90-4.99 (1H, m), 5.18 (2H, s), 6.85 (1H, s), 7.29-7.41 (5H, m), 7.55 (1H, s), 7.68-7.70 (2H, m), 7.78-7.80 (2H, m)

Reference Example 11-12

¹H-NMR (CDCl₃) δ ppm: 1.07 (3H, t, J=7.1 Hz), 3.99 (3H, s), 4.09 (2H, q, J=7.1 Hz), 5.19 (2H, s), 6.98 (1H, s), 7.00-7.10 (1H, m), 7.10-7.20 (1H, m), 7.25-7.50 (5H, m), 7.53 (1H, s), 7.60-7.70 (1H, m)

Reference Example 11-13

¹H-NMR (CDCl₃) δ ppm: 1.05 (3H, t, J=7.1 Hz), 3.99 (3H, s), 4.06 (2H, q, J=7.1 Hz), 5.19 (2H, s), 6.95 (1H, s), 7.25-7.60 (9H, m)

Reference Example 11-14

¹H-NMR (CDCl₃) δ ppm: 1.16 (3H, t, J=7.2 Hz), 4.00 (3H, s), 4.13 (2H, q, J=7.2 Hz), 5.20 (2H, s), 6.77 (1H, d, J=1.7 Hz), 7.04 (1H, s), 7.25-7.50 (5H, m), 7.53 (1H, s), 8.31 (1H, d, J=1.7 Hz)

Reference Example 11-15

¹H-NMR (CDCl₃) δ ppm: 1.19 (3H, t, J=7.1 Hz), 2.48 (3H, d, J=1.2 Hz), 3.98 (3H, s), 4.14 (2H, q, J=7.1 Hz), 5.18 (2H, s), 6.50-6.55 (1H, m), 7.08 (1H, s), 7.25-7.55 (6H, m)

Reference Example 11-16

¹H-NMR (CDCl₃) δ ppm: 1.13 (6H, d, J=6.3 Hz), 4.00 (3H, s), 4.96-5.05 (1H, m), 5.20 (2H, s), 6.76 (1H, d, J=1.8 Hz), 7.01 (1H, s), 7.33-7.47 (5H, m), 7.54 (1H, s), 8.31 (1H, d, J=1.8 Hz)

Reference Example 11-17

¹H-NMR (CDCl₃) δ ppm: 1.06 (3H, t, J=7.2 Hz), 3.90-4.10 (5H, m), 5.19 (2H, s), 7.14 (1H, s), 7.25-7.50 (5H, m), 7.54 (1H,$), 7.66 (1H, d, J=3.0 Hz), 7.93 (1H, d, J=3.0 Hz)

Reference Example 11-18

MS (ESI, m/z): 315 (M+H)+

Reference Example 11-19

¹H-NMR (CDCl₃) δ ppm: 1.11 (9H s), 1.35 (3H, t, J=7.1 Hz), 3.95 (3H, s), 4.31 (2H, q, J=7.1 Hz), 5.21 (2H, s), 6.57 (1H, s), 7.20-7.45 (5H, m), 7.50 (1H, s)

Reference Example 11-20

¹H-NMR (CDCl₃) δ ppm: 1.11 (9H, s), 1.33 (6H, d, J=6.3 Hz), 3.95 (3H, s), 5.15-5.21 (3H, m), 6.57 (1H, s), 7.25-7.40 (5H, m), 7.47 (1H, s)

Reference Example 11-21

MS (ESI, m/z): 383 (M+H)+

Reference Example 11-22

¹H-NMR (CDCl₃) δ ppm: 3.03-3.07 (2H, m), 3.22-3.26 (2H, m), 3.96 (3H, s), 5.18 (2H, s), 7.19-7.43 (12H, m)

Reference Example 11-23

¹H-NMR (CDCl₃) δ ppm: 1.14 (6H, d, J=6.9 Hz), 3.35-3.50 (1H, m), 3.97 (3H, s), 5.26 (2H, s), 7.20 (1H, s), 7.30-7.50 (6H, m)

Reference Example 11-24

MS (ESI, m/z): 324 (M+H)+

Reference Example 11-25

MS (ESI, m/z): 336 (M+H)+

Reference Example 11-26

¹H-NMR (CDCl₃) δ ppm: 1.39-1.87 (12H, m), 3.21-3.29 (1H, m), 3.97 (2H, s), 5.28 (2H, s), 7.20 (1H, s), 7.29 (1H, s), 7.32-7.45 (5H, m)

Reference Example 11-27

¹H-NMR (CDCl₃) δ ppm: 1.57-1.93 (4H, m), 3.29-3.51 (3H, m), 5.29 (2H, s), 7.20 (1H, s), 7.30 (1H, s), 7.32-7.44 (5H, m)

Reference Example 11-28

MS (ESI, m/z): 335 (M+H)+

Reference Example 11-29

MS (ESI, m/z): 349 (M+H)+

Reference Example 11-30

MS (ESI, m/z): 350 (M+H)+

Reference Example 11-31

MS (ESI, m/z): 350 (M+H)+

Reference Example 12-1

4-Benzyloxy-2-(2-fluorobenzoyl)-5-methoxybenzonitrile

A mixture of 5-benzyloxy-2-cyano-4-methoxybenzoic acid (reference example 5-3) (502 mg), 2-fluorophenylboronic acid (297 mg), tetrakis(triphenylphosphine)palladium (0) (205 mg), dimethylpyrocarbonate (2 mL) and 1,4-dioxane (10 mL) was stirred at 80° C. under an argon atmosphere for 1.25 hours. Ethyl acetate and Florisil (registered mark) (2 g) were added. After stirring for 15 minutes, the mixture was passed through a layer of Celite (registered mark). The filtrate was concentrated under reduced pressure. The residue was purified by silica gel column chromatography (eluent: 5%-30% ethyl acetate/hexane, gradient elution) to give the title compound (338 mg).

$^1$H-NMR (CDCl$_3$) δ ppm: 3.98 (3H, s), 5.16 (2H, s), 7.08-7.13 (1H, m), 7.21-7.22 (2H, m), 7.25-7.29 (1H, m), 7.34-7.35 (5H, m), 7.55-7.61 (2H, m)

Reference Example 13-1

2-Benzoyl-4-benzyloxy-5-methoxybenzonitrile

To a mixture of 5-benzyloxy-2-cyano-4,N-dimethoxy-N-methylbenzamide (reference example 6-2) (203 mg) and tetrahydrofuran (3.1 mL) was added phenylmagnesium bromide (1.08 mol/L tetrahydrofuran solution, 0.7 mL) under ice-bath cooling. The mixture was stirred for 1.5 hours. Phenylmagnesium bromide (1.08 mol/L tetrahydrofuran solution, 0.3 mL) was added to the mixture. After stirring under ice-bath cooling for 50 minutes, the mixture was stirred at room temperature overnight. Phenylmagnesium bromide (1.08 mol/L tetrahydrofuran solution, 0.35 mL) was added to the mixture. After stirring at 0° C. for 1.5 hours, to the mixture were added a saturated aqueous solution of ammonium chloride, 1 mol/L hydrochloric acid and ethyl acetate. The organic layer was washed with 1 mol/L hydrochloric acid, water and brine successively, and concentrated under reduced pressure. The residue was purified by silica gel column chromatography (eluent: 0%-30% ethyl acetate/hexane, gradient elution) to give the title compound (112 mg).

$^1$H-NMR (CDCl$_3$) δ ppm: 4.00 (3H, s), 5.18 (2H, s), 7.14 (1H, s), 7.25 (1H, s), 7.30-7.50 (7H, m), 7.55-7.70 (3H, m)

Reference Example 14-1

Isopropyl 2-(4-acetylbenzoyl)-4-benzyloxy-5-methoxybenzoate

A mixture of isopropyl 4-benzyloxy-2-(4-bromobenzoyl)-5-methoxybenzoate (reference example 11-7)(253 mg), 1-ethoxyvinyltri-N-butyltin (420 mg), tetrakis(triphenyl phosphine)palladium(0)(90 mg) and toluene (5 mL) was irradiated with microwave to heat at 180° C. for 10 min while stirring. The mixture was concentrated under reduced pressure. A mixture of the residue, 2 mol/L hydrochloric acid (5 mL) and tetrahydrofuran (5 mL) was stirred at room temperature for 30 minutes. The mixture was extracted with ethy acetate. The organic layer was washed with brine, dried over anhydrous magnesium sulfate and concentrated under reduced pressure. The residue was purified by silica gel column chromatography (eluent: 10%-100% ethyl acetate/hexane, gradient elution) to give the title compound (198 mg).

$^1$H-NMR (CDCl$_3$) δ ppm: 0.98 (6H, d, J=6.3 Hz), 2.63 (3H, s), 4.00 (3H, s), 4.88-4.98 (1H, m), 5.17 (2H, s), 6.88 (1H, s), 7.28-7.42 (5H, m), 7.56 (1H, s), 7.80 (2H, d, J=8.5 Hz), 7.97 (2H, d, J=8.5 Hz)

Reference Example 14-2

2-Acetyl-4-benzyloxy-5-methoxybenzonitrile

The title compound was prepared in a manner similar to those as described in reference example 14-1 using 4-benzyloxy-2-iodo-5-methoxybenzonitrile (reference example 3-1) instead of isopropyl 4-benzyloxy-2-(4-bromobenzoyl)-5-methoxybenzoate.

$^1$H-NMR (CDCl$_3$) δ ppm: 2.63 (3H, s), 3.97 (3H, s), 5.25 (2H, s), 7.19 (1H, s), 7.32-7.44 (5H, m), 7.45 (1H, s)

Reference Example 15-1

4-Benzyloxy-5-methoxy-2-(4-methylbenzoyl)benzonitrile

A mixture of (5-benzyloxy-2-bromo-4-methoxyphenyl)-p-tolylmethanone (reference example 10-1) (1.11 g), copper (I)cyanide (967 mg) and 1-methyl-2-pyrrolidinone (2 mL) was irradiated with microwave to heat at 200° C. for 10 min while stirring. Water, a 28% ammonia in water and ethyl acetate were added. The separated organic layer was dried over anhydrous magnesium sulfate, and concentrated under reduced pressure. The residue was triturated with diethyl ether to give the title compound (1.08 g).

$^1$H-NMR (CDCl$_3$) δ ppm: 2.44 (3H, s), 3.99 (3H, s), 5.17 (2H, s), 7.14 (1H, s), 7.20-7.25 (3H, m), 7.32-7.40 (5H, m), 7.58 (2H, d, J=8.3 Hz)

Reference Example 15-2

Isopropyl 4-benzyloxy-2-(2-cyanobenzoyl)-5-methoxybenzoate

A mixture of isopropyl 4-benzyloxy-2-(2-bromobenzoyl)-5-methoxybenzoate (reference example 11-9) (600 mg), copper(I) cyanide (445 mg), tris(dibenzylideneacetone)dipalladium (114 mg), tetraethylammonium cyanide (194 mg), 1,1'bis(diphenylphosphino)ferrocene (206 mg) and 1,4-dioxane (73 mL) was stirred under reflux overnight. The mixture was passed through a layer of Celite (registered mark). The filtrate was concentrated under reduced pressure. The residue was purified by silica gel column chromatography (eluent: 5%-30% ethyl acetate/hexane, gradient elution) to give the title compound (412 mg).

$^1$H-NMR (CDCl$_3$) δ ppm: 1.02 (6H, d, J=6.3 Hz), 4.00 (3H, s), 4.85-5.05 (1H, m), 5.19 (2H, s), 6.93 (1H, s), 7.20-7.50 (6H, m), 7.50-7.70 (3H, m), 7.80-7.90 (1H, m)

Reference examples 15-3 to 15-5 were prepared in a manner similar to those as described in reference example 15-1 or reference example 15-2 using the corresponding halobenzene instead of (5-benzyloxy-2-bromo-4-methoxyphenyl)-p-tolylmethanone or isopropyl-4-benzyloxy-2-(2-bromobenzoyl)-5-methoxybenzoate. These were illustrated in table 5.

TABLE 5

| Reference example | Structure |
| --- | --- |
| 15-1 | 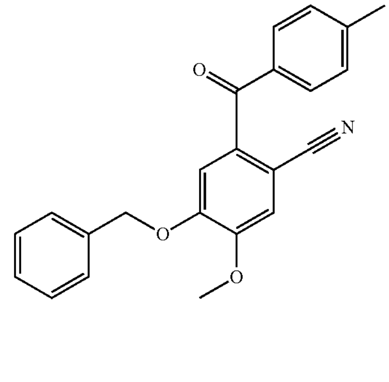 |

TABLE 5-continued

| Reference example | Structure |
|---|---|
| 15-2 | 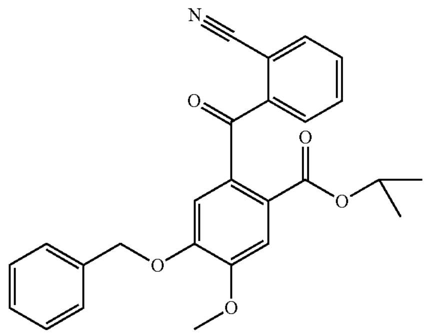 |
| 15-3 | 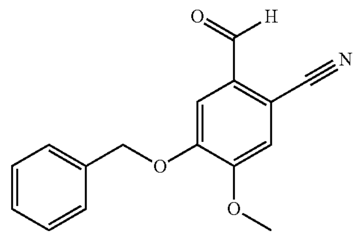 |
| 15-4 | 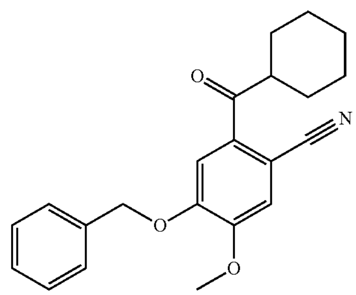 |
| 15-5 | 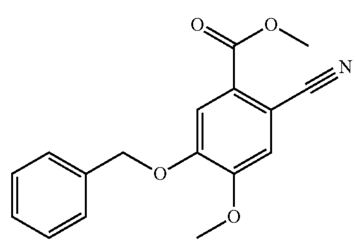 |

The physical data of reference example 15-3 to examples 15-5 were shown below.

Reference Example 15-3

$^1$H-NMR (CDCl$_3$) δ ppm: 4.00 (3H, s), 5.24 (2H, s), 7.19 (1H, s), 7.30-7.47 (5H, m), 7.54 (1H, s), 10.23 (1H, s)

Reference Example 15-4

$^1$H-NMR (CDCl$_3$) δ ppm: 1.29-1.86 (9H, m), 2.07-2.57 (1H, m), 3.02-3.56 (1H, m), 3.96 (3H, s), 5.26 (2H, s), 7.31-7.46 (6H, m)

Reference Example 15-5

$^1$H-NMR (CDCl$_3$) δ ppm: 3.96 (3H, s), 3.97 (3H, s), 5.23 (2H, s), 7.19 (1H, s), 7.30-7.50 (5H, m), 7.65 (1H, s)

Reference Example 16-1

2-Benzoyl-4-benzyloxy-5-methoxybenzoic acid

A mixture of ethyl 2-benzoyl-4-benzyloxy-5-methoxybenzoate (reference example 11-1) (947 mg), a 2 mol/L aqueous solution of sodium hydroxide (3.64 mL) and ethanol (12 mL) was stirred at 70° C. for 3 hours. Ethyl acetate and 2 mol/L hydrochloric acid were added to the mixture. The separated organic layer was washed with water and brine successively, dried over anhydrous magnesium sulfate, and concentrated under reduced pressure to give the title compound (0.87 g).

$^1$H-NMR (CDCl$_3$) δ ppm: 3.99 (3H, s), 5.17 (2H, s), 6.90 (1H, s), 7.29-7.44 (7H, m), 7.50-7.57 (1H, m), 7.61 (1H, s), 7.67-7.72 (2H, m)

Reference Examples 16-2 to 16-3 were prepared in a manner similar to those as described in Reference example 16-1 using the corresponding benzoate esters instead of ethyl 2-benzoyl-4-benzyloxy-5-methoxybenzoate. These were illustrated in table 6.

TABLE 6

| Reference example | Structure |
|---|---|
| 16-1 | 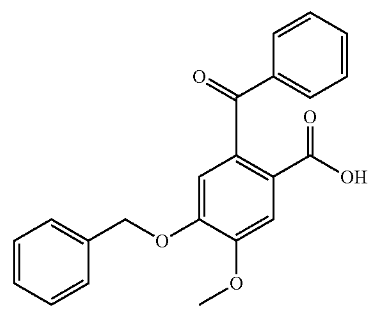 |
| 16-2 | 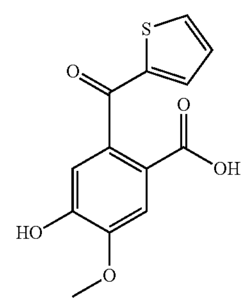 |
| 16-3 | 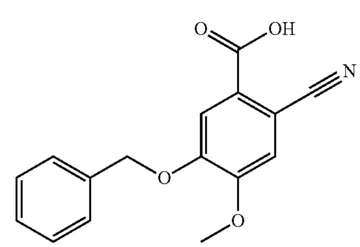 |

The physical data of reference example 16-2 to examples 16-3 were shown below.

Reference Example 16-2

$^1$H-NMR (DMSO-d$_6$) δ ppm: 3.88 (3H, s), 6.79 (1H, s), 7.11-7.19 (1H, m), 7.23-7.29 (1H, m), 7.44 (1H, s), 7.95-8.02 (1H, m), 10.23 (1H, s)

Reference Example 16-3

$^1$H-NMR (CDCl$_3$) δ ppm: 3.98 (3H, s), 5.24 (2H, s), 7.23 (1H, s), 7.30-7.50 (5H, m), 7.70 (1H, s)

Reference Example 17-1

Ethyl 2-benzoyl-4-hydroxy-5-methoxybenzoate

To a mixture of ethyl 2-benzoyl-4-benzyloxy-5-methoxybenzoate (reference example 11-1) (848 mg) and dichloromethane (30 mL) was added titanium tetrachloride (0.31 mL) under room temperature. After stirring for 30 minutes, 2 mol/L hydrochloric acid and ethyl acetate were added to the mixture. The separated organic layer was dried over anhydrous sodium sulfate, and concentrated under reduced pressure. The residue was purified by silica gel column chromatography (eluent: 10%-100% ethyl acetate/hexane, gradient elution) to give the title compound (550 mg).

$^1$H-NMR (CDCl$_3$) δ ppm: 0.98 (3H, t, J=7.2 Hz), 3.97-4.05 (5H, m), 7.38-7.45 (2H, m), 7.50-7.56 (2H, m), 7.73-7.79 (2H, m)

Reference Examples 17-2 to 17-46 were prepared in a manner similar to those as described in Reference example 17-1 using the corresponding benzyl ethers instead of ethyl 2-benzoyl-4-benzyloxy-5-methoxybenzoate. These were illustrated in table 7.

TABLE 7

| Reference example | Structure |
|---|---|
| 17-1 | 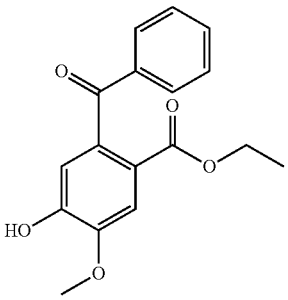 |
| 17-2 | 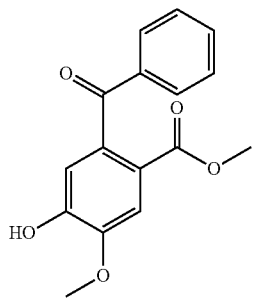 |

TABLE 7-continued

| Reference example | Structure |
|---|---|
| 17-3 | 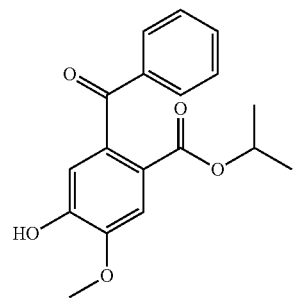 |
| 17-4 | 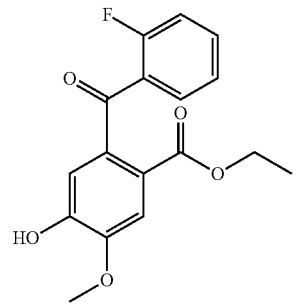 |
| 17-5 | 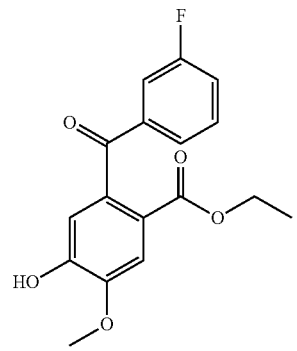 |
| 17-6 | 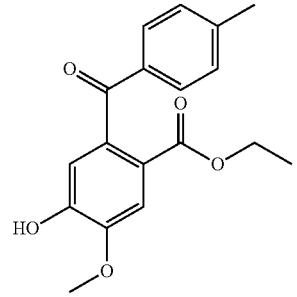 |

TABLE 7-continued
| Reference example | Structure |
|---|---|
| 17-7 |  |
| 17-8 |  |
| 17-9 | 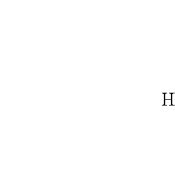 |
| 17-10 | 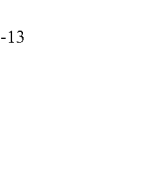 |
| 17-11 | 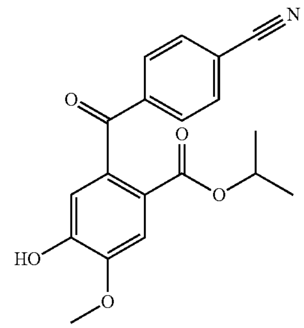 |
| 17-12 | 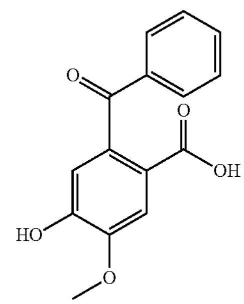 |
| 17-13 | 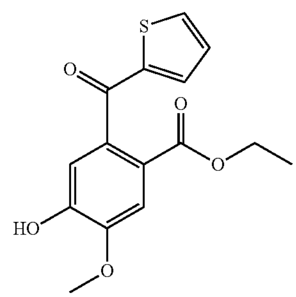 |
| 17-14 | 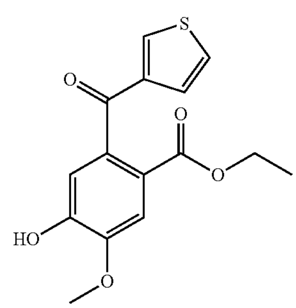 |
| 17-15 | 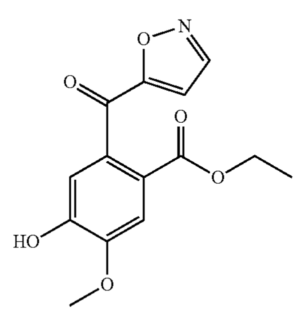 |

TABLE 7-continued

| Reference example | Structure |
|---|---|
| 17-16 | (5-methylisoxazol-3-yl ketone with ethyl ester, hydroxy, methoxy benzene) |
| 17-17 | (isoxazol-5-yl ketone with isopropyl ester, hydroxy, methoxy benzene) |
| 17-18 | (thiazol-2-yl ketone with ethyl ester, hydroxy, methoxy benzene) |
| 17-19 | (acetyl with methyl ester, hydroxy, methoxy benzene) |
| 17-20 | (pivaloyl with ethyl ester, hydroxy, methoxy benzene) |
| 17-21 | (pivaloyl with isopropyl ester, hydroxy, methoxy benzene) |
| 17-22 | (trifluoroacetyl with ethyl ester, hydroxy, methoxy benzene) |
| 17-23 | (piperidinyl amide with ethyl ester, hydroxy, methoxy benzene) |
| 17-24 | (piperidinyl amide with isopropyl ester, hydroxy, methoxy benzene) |
| 17-25 | (benzoyl with cyano, hydroxy, methoxy benzene) |

TABLE 7-continued

| Reference example | Structure |
|---|---|
| 17-26 | (4-methylphenyl)(4-hydroxy-5-methoxy-2-cyanophenyl)methanone |
| 17-27 | 1-(4-hydroxy-5-methoxy-2-cyanophenyl)-3-phenylpropan-1-one |
| 17-28 | (2-fluorophenyl)(4-hydroxy-5-methoxy-2-cyanophenyl)methanone |
| 17-29 | 1-(4-hydroxy-5-methoxy-2-cyanophenyl)ethan-1-one |
| 17-30 | 1-(4-hydroxy-5-methoxy-2-cyanophenyl)-2-methylpropan-1-one |
| 17-31 | 1-(4-hydroxy-5-methoxy-2-cyanophenyl)-2,2-dimethylpropan-1-one |
| 17-32 | cyclopentyl(4-hydroxy-5-methoxy-2-cyanophenyl)methanone |
| 17-33 | cyclohexyl(4-hydroxy-5-methoxy-2-cyanophenyl)methanone |
| 17-34 | cycloheptyl(4-hydroxy-5-methoxy-2-cyanophenyl)methanone |
| 17-35 | (tetrahydro-2H-pyran-4-yl)(4-hydroxy-5-methoxy-2-cyanophenyl)methanone |

TABLE 7-continued

| Reference example | Structure |
|---|---|
| 17-36 | (isoxazol-5-yl)(2-cyano-4-hydroxy-5-methoxyphenyl)methanone |
| 17-37 | (5-methylisoxazol-3-yl)(2-cyano-4-hydroxy-5-methoxyphenyl)methanone |
| 17-38 | (thiophen-3-yl)(2-cyano-4-hydroxy-5-methoxyphenyl)methanone |
| 17-39 | (thiophen-2-yl)(2-cyano-4-hydroxy-5-methoxyphenyl)methanone |
| 17-40 | N,N-diethyl-2-cyano-4-hydroxy-5-methoxybenzamide |
| 17-41 | (pyrrolidin-1-yl)(2-cyano-4-hydroxy-5-methoxyphenyl)methanone |
| 17-42 | (piperidin-1-yl)(2-cyano-4-hydroxy-5-methoxyphenyl)methanone |
| 17-43 | (azepan-1-yl)(2-cyano-4-hydroxy-5-methoxyphenyl)methanone |
| 17-44 | (morpholin-4-yl)(2-cyano-4-hydroxy-5-methoxyphenyl)methanone |
| 17-45 | ethyl 4-(2-cyano-4-hydroxy-5-methoxybenzoyl)piperazine-1-carboxylate |

TABLE 7-continued

| Reference example | Structure |
|---|---|
| 17-46 | (structure: methyl 2-cyano-4-methoxy-5-hydroxybenzoate) |

The physical data of reference example 17-2 to examples 17-46 were shown below.

Reference Example 17-2

$^1$H-NMR (CDCl$_3$) δ ppm: 3.54 (3H, s), 4.02 (3H, s), 6.95 (1H, s), 7.38-7.46 (2H, m), 7.50-7.56 (2H, m), 7.71-7.78 (2H, m)

Reference Example 17-3

$^1$H-NMR (CDCl$_3$) δ ppm: 0.95 (6H, d, J=6.3 Hz), 4.02 (3H, s), 4.89-4.98 (1H, m), 6.90 (1H, s), 7.37-7.46 (2H, m), 7.49-7.58 (2H, m), 7.74-7.81 (2H, m)

Reference Example 17-4

$^1$H-NMR (CDCl$_3$) δ ppm: 1.09 (3H, t, J=7.2 Hz), 4.01 (3H, s), 4.10 (2H, q, J=7.2 Hz), 6.02 (1H, s), 6.93 (1H, s), 7.00-7.15 (1H, m), 7.15-7.25 (1H, m), 7.45-7.60 (2H, m), 7.70-7.85 (1H, m)

Reference Example 17-5

$^1$H-NMR (CDCl$_3$) δ ppm: 1.04 (3H, t, J=7.2 Hz), 3.95-4.15 (5H, m), 6.08 (1H, s), 6.91 (1H, s), 7.15-7.70 (5H, m)

Reference Example 17-6

$^1$H-NMR (CDCl$_3$) δ ppm: 1.00 (3H, t, J=7.2 Hz), 2.40 (3H, s), 3.95-4.10 (5H, m), 6.04 (1H, s), 6.91 (1H, s), 7.15-7.25 (2H, m), 7.54 (1H, s), 7.60-7.70 (2H, m)

Reference Example 17-7

$^1$H-NMR (CDCl$_3$) δ ppm: 0.98 (6H, d, J=6.3 Hz), 2.64 (3H, s), 4.03 (3H, s), 4.89-4.99 (1H, m), 6.90 (1H, s), 7.57 (1H, s), 7.86 (1H, d, J=8.5 Hz), 7.99 (1H, d, J=8.5 Hz)

Reference Example 17-8

$^1$H-NMR (CDCl$_3$) δ ppm: 0.96 (6H, d, J=6.3 Hz), 3.94 (3H, s), 4.03 (3H, s), 4.85-5.05 (1H, m), 6.07 (1H, s), 6.90 (1H, s), 7.57 (1H, s), 7.75-7.90 (2H, m), 8.00-8.15 (2H, m)

Reference Example 17-9

$^1$H-NMR (CDCl$_3$) δ ppm: 1.03 (6H, d, J=6.3 Hz), 4.03 (3H, s), 4.90-5.05 (1H, m), 6.07 (1H, s), 6.94 (1H, s), 7.50-7.70 (4H, m), 7.80-7.95 (1H, m)

Reference Example 17-10

$^1$H-NMR (CDCl$_3$) δ ppm: 1.04 (6H, d, J=6.3 Hz), 4.04 (3H, s), 4.91-5.02 (1H, m), 6.88 (1H, s), 7.55-7.61 (2H, m), 7.79-7.84 (1H, m), 7.96-7.99 (1H, m), 8.04-8.08 (1H, m)

Reference Example 17-11

$^1$H-NMR (CDCl$_3$) δ ppm: 1.02 (6H, d, J=6.2 Hz), 4.03 (3H, s), 4.92-5.00 (1H, m), 6.09 (1H, s), 6.88 (1H, s), 7.56 (1H, s), 7.70-7.74 (2H, m), 7.85-7.88 (2H, m)

Reference Example 17-12

$^1$H-NMR (DMSO-d$_6$) δ ppm: 3.95 (3H, s), 6.79 (1H, s), 7.50-7.56 (3H, m), 7.61-7.69 (3H, m)

Reference Example 17-13

$^1$H-NMR (CDCl$_3$) δ ppm: 1.07 (3H, t, J=7.2 Hz), 4.02 (3H, s), 4.10 (2H, q, J=7.2 Hz), 6.04 (1H, s), 7.00 (1H, s), 7.00-7.10 (1H, m), 7.25-7.35 (1H, m), 7.54 (1H, s), 7.60-7.70 (1H, m)

Reference Example 17-14

$^1$H-NMR (CDCl$_3$) δ ppm: 1.05 (3H, t, J=7.2 Hz), 4.01 (3H, s), 4.07 (2H, q, J=7.2 Hz), 6.03 (1H, s), 6.97 (1H, s), 7.25-7.40 (1H, m), 7.45-7.60 (2H, m), 7.60-7.70 (1H, m)

Reference Example 17-15

$^1$H-NMR (CDCl$_3$) δ ppm: 1.16 (3H, t, J=7.1 Hz), 4.03 (3H, s), 4.13 (2H, q, J=7.1 Hz), 6.09 (1H, s), 6.80-6.90 (1H, m), 7.05 (1H, s), 7.54 (1H, s), 8.30-8.40 (1H, m)

Reference Example 17-16

$^1$H-NMR (CDCl$_3$) δ ppm: 1.18 (3H, t, J=7.2 Hz) 2.48 (3H, d, J=0.6 Hz), 4.00 (3H, s), 4.14 (2H, q, J=7.2 Hz), 6.02 (1H, s), 6.50-6.60 (1H, m), 7.05 (1H, s), 7.50 (1H, s)

Reference Example 17-17

$^1$H-NMR (CDCl$_3$) δ ppm: 1.13 (6H, d, J=6.3 Hz), 4.03 (3H, s), 4.97-5.06 (1H, m), 6.10 (1H, s), 6.83 (1H, d, J=1.9 Hz), 7.02 (1H, s), 7.54 (1H, s), 8.33 (1H, d, J=1.9 Hz)

Reference Example 17-18

$^1$H-NMR (CDCl$_3$) δ ppm: 1.06 (3H, t, J=7.2 Hz), 3.95-4.10 (5H, m), 6.02 (1H, s), 7.11 (1H, s), 7.55 (1H, s), 7.66 (1H, d, J=3.1 Hz), 7.93 (1H, d, J=3.1 Hz)

Reference Example 17-19

$^1$H-NMR (CDCl$_3$) δ ppm: 2.49 (3H, s), 3.87 (3H, s), 3.97 (3H, s), 6.02 (1H, s), 6.94 (1H, s), 7.34 (1H, s)

Reference Example 17-20

$^1$H-NMR (CDCl$_3$) δ ppm: 1.24 (9H, s), 1.35 (3H, t, J=7.2 Hz), 3.97 (3H, s), 4.32 (2H, q, J=7.2 Hz), 6.03 (1H, s), 6.72 (1H, s), 7.49 (1H, s)

Reference Example 17-21

¹H-NMR (CDCl₃) δ ppm: 1.24 (9H,$), 1.34 (6H, d, J=6.3 Hz), 3.97 (3H, s), 5.15-5.24 (1H, m), 6.01 (1H, s), 6.72 (1H, s), 7.46 (1H, s)

Reference Example 17-22

¹H-NMR (CDCl₃) δ ppm: 1.36 (3H, t, J=7.1 Hz), 4.02 (3H, s), 4.38 (2H, q, J=7.1 Hz), 6.11 (1H, brs), 6.96 (1H, s), 7.50 (1H, s)

Reference Example 17-23

¹H-NMR (CDCl₃) δ ppm: 1.35 (3H, t, J=7.0 Hz), 1.40-1.75 (6H, m), 3.00-3.58 (3H, m), 3.90-4.10 (4H, m), 4.32 (2H, q, J=7.0 Hz), 6.27 (1H, s), 6.80 (1H, s), 7.51 (1H, s)

Reference Example 17-24

¹H-NMR (CDCl₃) δ ppm: 1.32 (6H, d, J=6.3 Hz), 1.36-1.81 (6H, m), 2.92-3.36 (3H, m), 3.93-4.24 (4H, m), 5.14-5.24 (1H, m), 6.31 (1H, s), 6.79 (1H, s), 7.50 (1H, s)

Reference Example 17-25

¹H-NMR (CDCl₃) δ ppm: 4.03 (3H, s), 6.09 (1H, brs), 7.20 (1H, s), 7.25 (1H, s), 7.45-7.55 (2H, m), 7.55-7.70 (1H, m), 7.75-7.85 (2H, m)

Reference Example 17-26

¹H-NMR (CDCl₃) δ ppm: 2.44 (3H, s), 4.02 (3H, s), 7.19 (1H, s), 7.24 (1H, s), 7.29 (2H, d, J=8.1 Hz), 7.71 (2H, d, J=8.1 Hz)

Reference Example 17-27

¹H-NMR (CDCl₃) δ ppm: 3.06-3.10 (2H, m), 3.25-3.29 (2H, m), 4.00 (3H, s), 6.05 (1H, s), 7.19-7.30 (6H, m), 7.43 (1H, s)

Reference Example 17-28

¹H-NMR (CDCl₃) δ ppm: 4.02 (3H, s), 6.08 (1H, s), 7.12-7.17 (1H, m), 7.22-7.23 (1H, m), 7.24 (1H, s), 7.28-7.32 (1H, m), 7.55-7.61 (1H, m), 7.63-7.67 (1H, m)

Reference Example 17-29

¹H-NMR (DMSO-d₆) δ ppm: 2.55 (3H, s), 3.90 (3H, s), 7.46 (1H, s), 7.49 (1H, s), 10.53 (1H, s)

Reference Example 17-30

¹H-NMR (CDCl₃) δ ppm: 1.22 (6H, d, J=6.8 Hz), 3.35-3.55 (1H, m), 4.00 (3H, s), 6.08 (1H, s), 7.22 (1H, s), 7.42 (1H, s)

Reference Example 17-31

¹H-NMR (CDCl₃) δ ppm: 1.31 (9H, s), 3.97 (3H, s), 6.10 (1H, s), 7.01 (1H, s), 7.14 (1H, s)

Reference Example 17-32

¹H-NMR (CDCl₃) δ ppm: 1.50-1.85 (4H, m), 1.85-2.05 (4H, m), 3.50-3.70 (1H, m), 4.00 (3H, s), 6.06 (1H, brs), 7.22 (1H, s), 7.47 (1H, s)

Reference Example 17-33

¹H-NMR (CDCl₃) δ ppm: 1.30-1.94 (10H, m), 3.11-3.23 (1H, m), 3.98 (3H, s), 7.20 (1H, s), 7.41 (1H, s)

Reference Example 17-34

¹H-NMR (CDCl₃) δ ppm: 1.47-1.99 (12H, m), 3.28-3.39 (1H, m), 4.00 (3H, s), 7.21 (1H, s), 7.39 (1H, s)

Reference Example 17-35

¹H-NMR (CDCl₃) δ ppm: 1.89-2.08 (4H, m), 2.80-2.94 (1H, m), 3.45-3.56 (2H, m), 3.93 (3H, s), 3.99-4.09 (2H, m), 6.80 (1H, s), 7.03 (1H, s)

Reference Example 17-36

¹H-NMR (CDCl₃) δ ppm: 4.06 (3H, s), 6.14 (1H, s), 7.13 (1H, d, J=2.0 Hz), 7.30 (1H, s), 7.71 (1H, s), 8.44 (1H, d, J=2.0 Hz)

Reference Example 17-37

¹H-NMR (CDCl₃) δ ppm: 2.50-2.60 (3H, m), 4.03 (3H, s), 6.07 (1H, s), 6.50-6.60 (1H, m), 7.27 (1H, s), 7.95 (1H, s)

Reference Example 17-38

MS (ESI, m/z): 260 (M+H)+

Reference Example 17-39

¹H-NMR (CDCl₃) δ ppm: 4.03 (3H, s), 6.13 (1H, s), 7.10-7.20 (1H, m), 7.25 (1H, s), 7.35 (1H, s), 7.55-7.65 (1H, m), 7.75-7.85 (1H, m)

Reference Example 17-40

¹H-NMR (CDCl₃) δ ppm: 1.12 (3H, t, J=7.2 Hz), 1.28 (3H, t, J=7.2 Hz), 3.23 (2H, q, J=7.2 Hz), 3.58 (2H, q, J=7.2 Hz), 3.96 (3H, s), 6.19 (1H, s), 6.94 (1H, s), 7.09 (1H, s)

Reference Example 17-41

¹H-NMR (DMSO-d₆) δ ppm: 1.78-1.91 (4H, m), 3.22 (2H, t, J=6.4 Hz), 3.45 (2H, t, J=6.8 Hz), 3.84 (3H, s), 6.88 (1H, s), 7.40 (1H, s), 10.53 (1H, br s)

Reference Example 17-42

¹H-NMR (DMSO-d₆) δ ppm: 1.46-1.61 (6H, m), 3.08-3.23 (2H, m), 3.58 (2H, brs), 3.84 (3H, s), 6.79 (1H, s), 7.41 (1H, s), 10.57 (1H, br s)

Reference Example 17-43

¹H-NMR (CDCl₃) δ ppm: 1.54-1.69 (6H, m), 1.83-1.89 (2H, m), 3.31-3.34 (2H, m), 3.69-3.72 (2H, m), 3.95 (3H, s), 6.32 (1H, s), 6.93 (1H, s), 7.09 (1H, s)

Reference Example 17-44

¹H-NMR (DMSO-d₆) δ ppm: 3.17-3.27 (2H, m), 3.48-3.72 (6H, m), 3.84 (3H, s), 6.84 (1H, s), 7.43 (1H, s), 10.63 (1H, br s)

Reference Example 17-45

¹H-NMR (CDCl₃) δ ppm: 1.27 (3H, t, J=7.1 Hz), 3.23-3.40 (2H, m), 3.45-3.70 (4H, m), 3.70-3.90 (2H, m), 3.97 (3H, s), 4.17 (2H, q, J=7.1 Hz), 6.21 (1H, s), 6.98 (1H, s), 7.11 (1H, s)

Reference Example 17-46

¹H-NMR (CDCl₃) δ ppm: 3.97 (3H, s), 4.00 (3H, s), 6.05 (1H, s), 7.20 (1H, s), 7.66 (1H, s)

Reference Example 18-1

Ethyl 2-benzoyl-4-hydroxy-5-methoxy-3-nitrobenzoate

To a mixture of ethyl 2-benzoyl-4-hydroxy-5-methoxybenzoate (reference example 17-1) (550 mg) and dichloromethane (10 mL) was added fuming nitric acid (85 μL) at room temperature. After stirring for 20 minutes, water and dichloromethane were added to the mixture. The separated organic layer was brine, dried over anhydrous sodium sulfate, and concentrated under reduced pressure to give the title compound (806 mg).

¹H-NMR (CDCl₃) δ ppm: 1.26 (3H, t, J=7.2 Hz), 4.07 (3H, s), 4.12 (2H, q, J=7.2 Hz), 7.41-7.47 (2H, m), 7.52-7.59 (1H, m), 7.74-7.82 (2H, m), 10.81 (1H, s)

Reference Examples 18-2 to 18-47 were prepared in a manner similar to those as described in Reference example 18-1 using the corresponding phenols instead of ethyl 2-benzoyl-4-hydroxy-5-methoxybenzoate. These were illustrated in table 8.

TABLE 8

| Reference example | Structure |
|---|---|
| 18-1 | |
| 18-2 | 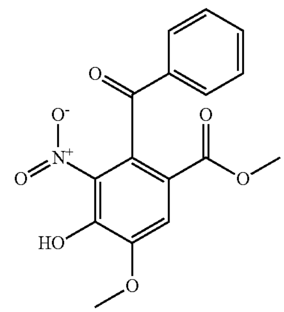 |
| 18-3 | 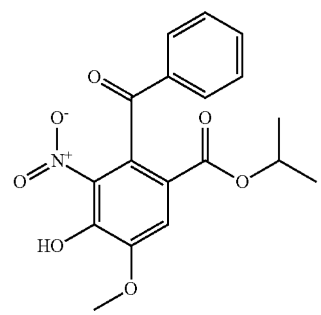 |
| 18-4 | 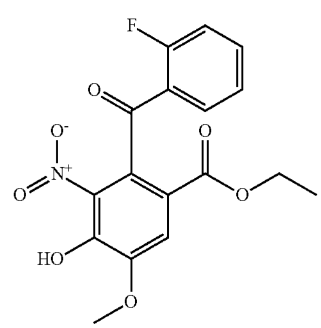 |
| 18-5 | 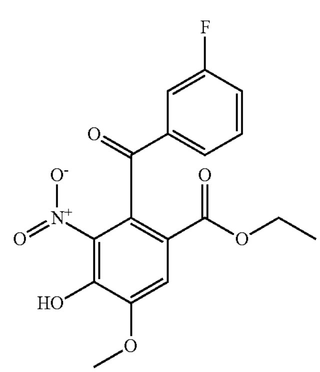 |

TABLE 8-continued

| Reference example | Structure |
|---|---|
| 18-6 | (structure) |
| 18-7 | (structure) |
| 18-8 | (structure) |
| 18-9 | (structure) |
| 18-10 | (structure) |
| 18-11 | (structure) |
| 18-12 | (structure) |
| 18-13 | (structure) |
| 18-14 | (structure) |

TABLE 8-continued

| Reference example | Structure |
|---|---|
| 18-15 | 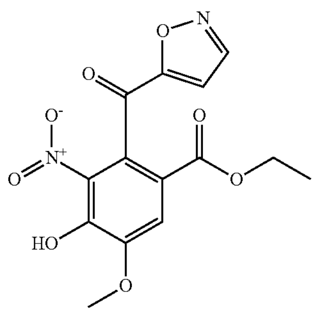 |
| 18-16 | 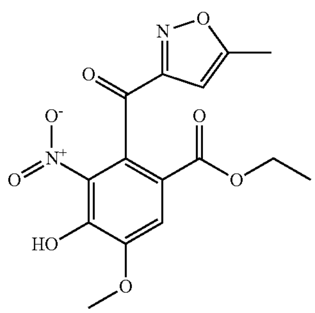 |
| 18-17 | 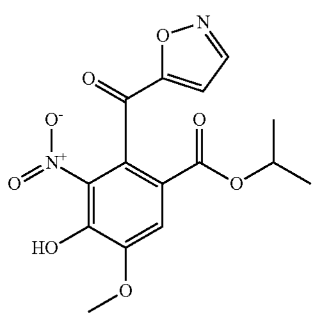 |
| 18-18 | 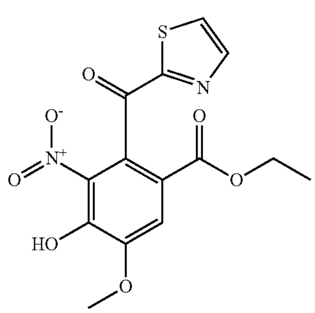 |
| 18-19 | 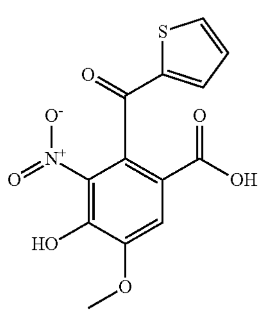 |
| 18-20 | |
| 18-21 | |
| 18-22 | |
| 18-23 | |
| 18-24 | |

TABLE 8-continued

| Reference example | Structure |
|---|---|
| 18-25 | 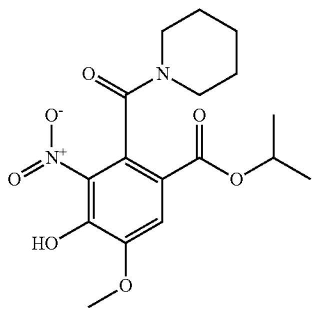 |
| 18-26 | 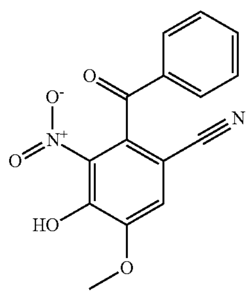 |
| 18-27 | 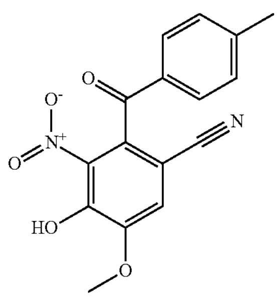 |
| 18-28 | 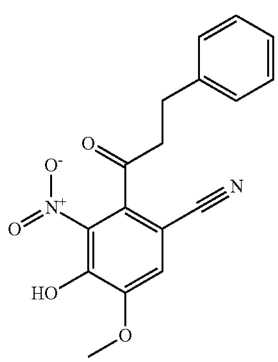 |
| 18-29 | 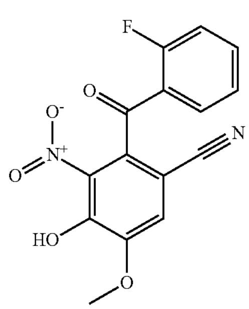 |
| 18-30 | |
| 18-31 | |
| 18-32 | |
| 18-33 | |
| 18-34 | |

TABLE 8-continued

| Reference example | Structure |
|---|---|
| 18-35 | (cycloheptyl ketone with 2-nitro-3-hydroxy-4-methoxy-6-cyanophenyl) |
| 18-36 | (tetrahydropyran-4-yl ketone with 2-nitro-3-hydroxy-4-methoxy-6-cyanophenyl) |
| 18-37 | (isoxazol-5-yl ketone with 2-nitro-3-hydroxy-4-methoxy-6-cyanophenyl) |
| 18-38 | (5-methylisoxazol-3-yl ketone with 2-nitro-3-hydroxy-4-methoxy-6-cyanophenyl) |
| 18-39 | (thiophen-3-yl ketone with 2-nitro-3-hydroxy-4-methoxy-6-cyanophenyl) |
| 18-40 | (thiophen-2-yl ketone with 2-nitro-3-hydroxy-4-methoxy-6-cyanophenyl) |
| 18-41 | (N,N-diethylamide with 2-nitro-3-hydroxy-4-methoxy-6-cyanophenyl) |
| 18-42 | (pyrrolidine amide with 2-nitro-3-hydroxy-4-methoxy-6-cyanophenyl) |
| 18-43 | (piperidine amide with 2-nitro-3-hydroxy-4-methoxy-6-cyanophenyl) |
| 18-44 | (azepane amide with 2-nitro-3-hydroxy-4-methoxy-6-cyanophenyl) |

TABLE 8-continued

| Reference example | Structure |
|---|---|
| 18-45 | (structure) |
| 18-46 | (structure) |
| 18-47 | (structure) |

The physical data of reference example 18-2 to examples 18-47 were shown below.

Reference Example 18-2

$^1$H-NMR (CDCl$_3$) δ ppm: 3.64 (3H, s), 4.07 (3H, s), 7.42-7.48 (2H, m), 7.53-7.59 (1H, m), 7.75-7.80 (3H, m), 10.85 (1H, s)

Reference Example 18-3

$^1$H-NMR (CDCl$_3$) δ ppm: 0.90-1.02 (6H, m), 4.07 (3H, s), 4.94-5.03 (1H, m), 7.41-7.48 (2H, m), 7.52-7.59 (1H, m), 7.76-7.84 (3H, m), 10.82-10.84 (1H, m)

Reference Example 18-4

$^1$H-NMR (DMSO-d$_6$) δ ppm: 0.99 (3H, t, J=7.0 Hz), 3.95-4.10 (5H, m), 7.20-7.45 (2H, m), 7.61 (1H, s), 7.65-7.80 (2H, m)

Reference Example 18-5

$^1$H-NMR (DMSO-d$_6$) δ ppm: 0.95 (3H, t, J=7.0 Hz), 3.90-4.10 (5H, m), 7.40-7.70 (5H, m)

Reference Example 18-6

$^1$H-NMR (DMSO-d$_6$) δ ppm: 0.93 (3H, t, J=7.1 Hz), 2.38 (3H, s), 3.94 (2H, q, J=7.1 Hz), 4.02 (3H, s), 7.25-7.40 (2H, m), 7.50-7.70 (3H, m)

Reference Example 18-7

$^1$H-NMR (CDCl$_3$) δ ppm: 0.95-1.06 (6H, m), 2.65 (3H, s), 4.08 (3H, s), 4.94-5.06 (1H, m), 7.81 (1H, s), 7.85-7.92 (2H, m), 8.01-8.05 (2H, m), 10.87-10.89 (1H, m)

Reference Example 18-8

$^1$H-NMR (DMSO-d$_6$) δ ppm: 0.89 (6H, d, J=6.3 Hz), 3.89 (3H, s), 4.04 (3H, s), 4.70-4.90 (1H, m), 7.65 (1H, s), 7.75-7.95 (2H, m), 8.00-8.20 (2H, m)

Reference Example 18-9

$^1$H-NMR (DMSO-d$_6$) δ ppm: 0.75-1.10 (6H, m), 4.02 (3H, s), 4.75-4.90 (1H, m), 7.61 (1H, s), 7.65-7.90 (3H, m), 8.00-8.15 (1H, m)

Reference Example 18-10

MS (ESI, m/z): 383 (M−H)−

Reference Example 18-11

$^1$H-NMR (CDCl$_3$) δ ppm: 1.04 (6H, d, J=6.1 Hz), 4.08 (3H, s), 4.97-5.06 (1H, m), 7.74-7.77 (2H, m), 7.80 (1H, s), 7.88-7.91 (2H, m), 10.84 (1H, s)

Reference Example 18-12

$^1$H-NMR (DMSO-d$_6$) δ ppm: 4.00 (1H, s), 7.44-7.54 (2H, m), 7.57-7.67 (3H, m), 7.70-7.76 (1H, m)

Reference Example 18-13

$^1$H-NMR (DMSO-d$_6$) δ ppm: 0.98 (3H, t, J=7.2 Hz), 3.90-4.15 (5H, m), 7.10-7.25 (1H, m), 7.35-7.45 (1H, m), 7.62 (1H, s), 8.05-8.15 (1H, m)

Reference Example 18-14

$^1$H-NMR (DMSO-d$_6$) δ ppm: 0.53 (3H, t, J=7.1 Hz), 3.90-4.10 (5H, m), 7.35-7.45 (1H, m), 7.60 (1H, s), 7.60-7.70 (1H, m), 7.95-8.10 (1H, m), 11.40-12.00 (1H, br)

Reference Example 18-15

$^1$H-NMR (DMSO-d$_6$) δ ppm: 1.08 (3H, t, J=7.1 Hz), 4.03 (3H, s), 4.10 (2H, q, J=7.1 Hz), 7.21 (1H, d, J=2.0 Hz), 7.65 (1H, s), 8.83 (1H, d, J=2.0 Hz)

Reference Example 18-16

$^1$H-NMR (DMSO-d$_6$) δ ppm: 1.09 (3H, t, J=7.2 Hz), 4.02 (3H, s), 4.09 (2H, q, J=7.2 Hz), 6.70-6.80 (1H, m), 7.60 (1H, s), 11.00-12.50 (1H, br)

Reference Example 18-17

$^1$H-NMR (DMSO-d$_6$) δ ppm: 1.06 (6H, d, J=6.3 Hz), 4.03 (3H, s), 4.85-4.95 (1H, m), 7.22 (1H, d, J=2.0 Hz), 7.63 (1H, s), 8.84 (1H, d, J=2.0 Hz), 11.94 (1H, br s)

Reference Example 18-18

$^1$H-NMR (DMSO-d$_6$) δ ppm: 0.98 (3H, t, J=7.2 Hz), 3.90-4.10 (5H, m), 7.61 (1H, s), 8.05 (1H, d, J=3.0 Hz), 8.26 (1H, d, J=3.0 Hz), 11.50-12.50 (1H, br)

Reference Example 18-19

$^1$H-NMR (DMSO-d$_6$) δ ppm: 4.00 (3H, s), 7.12-7.17 (1H, m), 7.32-7.37 (1H, m), 7.61 (1H, s), 7.99-8.04 (1H, m), 11.65 (1H, br. s.)

Reference Example 18-20

MS (ESI, m/z): 268 (M–H)–

Reference Example 18-21

$^1$H-NMR (DMSO-d$_6$) δ ppm: 1.09 (9H, s), 1.30 (3H, t, J=7.0 Hz), 3.96 (3H, s), 4.15-4.45 (2H, m), 7.57 (1H, s), 11.50-12.00 (1H, br)

Reference Example 18-22

$^1$H-NMR (DMSO-d$_6$) δ ppm: 1.09 (9H,$), 1.32 (6H, d, J=6.3 Hz), 3.97 (3H, s), 5.02-5.11 (1H, m), 7.53 (1H, s), 11.70 (1H, br s)

Reference Example 18-23

$^1$H-NMR (DMSO-d$_6$) δ ppm: 1.32 (3H, t, J=7.0 Hz), 4.02 (3H, s), 4.37 (2H, q, J=7.0 Hz), 7.62 (1H, s)

Reference Example 18-24

$^1$H-NMR (DMSO-d$_6$) δ ppm: 1.27 (3H, t, J=7.0 Hz), 1.35-1.67 (6H, m), 2.94-3.28 (3H, m), 3.66-3.73 (1H, m), 3.96 (3H, s), 4.26 (2H, q, J=7.0 Hz), 7.58 (1H, s), 11.61 (1H, br s)

Reference Example 18-25

$^1$H-NMR (CDCl$_3$) δ ppm: 1.10-1.80 (12H, m), 3.03-3.40 (3H, m), 4.01 (3H, s), 4.06-4.13 (1H, m), 5.17-5.26 (1H, m), 7.67 (1H, s), 10.07 (1H, br s)

Reference Example 18-26

$^1$H-NMR (DMSO-d$_6$) δ ppm: 4.00 (3H, s), 7.50-7.65 (2H, m), 7.70-7.90 (4H, m)

Reference Example 18-27

$^1$H-NMR (CDCl$_3$) δ ppm: 2.44 (3H, s), 4.05 (3H, s), 7.27-7.33 (3H, m), 7.67 (2H, d, J=8.3 Hz)

Reference Example 18-28

$^1$H-NMR (DMSO-d$_6$) δ ppm: 2.90-2.94 (2H, m), 3.20-3.24 (2H, m), 3.98 (3H, s), 7.14-7.31 (5H, m), 7.74 (1H, s)

Reference Example 18-29

$^1$H-NMR (DMSO-d$_6$) δ ppm: 3.99 (3H, s), 7.37-7.42 (2H, m), 7.73-7.82 (3H, m)

Reference Example 18-30

$^1$H-NMR (CDCl$_3$) δ ppm: 2.66 (3H, s), 4.02 (3H, s), 7.25 (1H, s)

Reference Example 18-31

$^1$H-NMR (DMSO-d$_6$) δ ppm: 1.11 (6H, d, J=6.8 Hz), 3.00-3.15 (1H, m), 3.97 (3H, s), 7.71 (1H, s)

Reference Example 18-32

$^1$H-NMR (DMSO-d$_6$) δ ppm: 1.17 (9H, s), 3.93 (3H, s), 7.66 (1H, s)

Reference Example 18-33

$^1$H-NMR (DMSO-d$_6$) δ ppm: 1.45-1.95 (8H, m), 3.25-3.50 (1H, m), 3.97 (3H, s), 7.70 (1H, s)

Reference Example 18-34

$^1$H-NMR (CDCl$_3$) δ ppm: 1.50-2.01 (10H, m), 2.52-2.65 (1H, m), 4.01 (3H, s), 7.27 (1H, s)

Reference Example 18-35

$^1$H-NMR (CDCl$_3$) δ ppm: 1.41-1.61 (6H, m), 1.73-1.86 (4H, m), 1.97-2.07 (2H, m), 2.71-2.81 (1H, m), 7.27 (1H, s), 10.81 (1H, s)

Reference Example 18-36

$^1$H-NMR (DMSO-d$_6$) δ ppm: 1.50-1.63 (2H, m), 1.68-1.76 (2H, m), 3.07-3.18 (1H, m), 3.29-3.38 (2H, m), 3.84-3.92 (2H, m), 3.98 (3H, s), 7.78 (1H, s)

Reference Example 18-37

$^1$H-NMR (DMSO-d$_6$) δ ppm: 3.98 (3H, s), 7.44 (1H, d, J=2.0 Hz), 7.70 (1H, s), 8.93 (1H, d, J=2.0 Hz)

Reference Example 18-38

$^1$H-NMR (DMSO-d$_6$) δ ppm: 2.45-2.55 (3H, m), 4.00 (3H, s), 6.85-6.90 (1H, m), 7.78 (1H, s)

Reference Example 18-39

$^1$H-NMR (DMSO-d$_6$) δ ppm: 3.98 (3H, s), 7.45-7.55 (1H, m), 7.65-7.80 (2H, m), 8.30-8.40 (1H, m)

Reference Example 18-40

$^1$H-NMR (DMSO-d$_6$) δ ppm: 4.00 (3H, s), 7.20-7.35 (1H, m), 7.60-7.70 (1H, m), 7.78 (1H, s), 8.20-8.30 (1H, m)

Reference Example 18-41

$^1$H-NMR (DMSO-d$_6$) δ ppm: 1.08-1.13 (6H, m), 3.19-3.25 (2H, m), 3.39-3.47 (2H, m), 3.95 (3H, s), 7.71 (1H, s), 12.14 (1H, br s)

Reference Example 18-42

$^1$H-NMR (DMSO-d$_6$) δ ppm: 1.80-1.94 (4H, m), 3.20-3.46 (4H, m), 3.96 (3H, s), 7.72 (1H, s), 12.14 (1H, br s)

Reference Example 18-43

$^1$H-NMR (DMSO-$d_6$) δ ppm: 1.53-1.64 (6H, m), 3.50-3.61 (2H, m), 3.95 (3H, s), 7.70 (1H, s)

Reference Example 18-44

$^1$H-NMR (DMSO-$d_6$) δ ppm: 1.50-1.73 (8H, m), 3.24-3.58 (4H, m), 3.95 (3H, s), 7.71 (1H, s)

Reference Example 18-45

$^1$H-NMR (DMSO-$d_6$) δ ppm: 3.26-3.68 (8H, m), 3.95 (3H, s), 7.73 (1H, s)

Reference Example 18-46

$^1$H-NMR (DMSO-$d_6$) δ ppm: 1.19 (3H, t, J=7.1 Hz), 3.29-3.68 (8H, m), 3.95 (3H, s), 4.07 (2H, q, J=7.1 Hz), 7.73 (1H, s)

Reference Example 18-47

$^1$H-NMR (CDCl$_3$) δ ppm: 4.01 (3H, s), 4.04 (3H, s), 7.25 (1H, s), 9.56 (1H, br s)

Example 1-1

Ethyl 2-benzoyl-4,5-dihydroxy-3-nitrobenzoate (compound 1-1)

To a mixture of ethyl 2-benzoyl-4-hydroxy-5-methoxy-3-nitrobenzoate (reference example 18-1) (806 mg) and ethyl acetate (10 mL) were added aluminum chloride (610 mg) and pyridine (0.889 mL). The mixture was stirred at 77° C. for 2 hours. After cooling to room temperature, 2 mol/L hydrochloric acid was added to the mixture. The separated organic layer was washed with brine successively, dried over anhydrous magnesium sulfate, and concentrated under reduced pressure. The residue was triturated with hexane:diethyl ether=4:1 to give the title compound (430 mg).

$^1$H-NMR (DMSO-$d_6$) δ ppm: 0.91 (3H, t, J=7.1 Hz), 3.91 (2H, q, J=7.1 Hz), 7.45-7.52 (3H, m), 7.56 (1H, s), 7.59-7.68 (2H, m)

Compounds 1-2 to 1-47 were prepared in a manner similar to those as described in example 1-1 using the corresponding 3-nitrobenzene-1-methoxy-2-ol instead of ethyl 2-benzoyl-4-hydroxy-5-methoxy-3-nitrobenzoate. These were illustrated in table 9.

TABLE 9

| Compound No. | Structure |
|---|---|
| 1-1 | ethyl 2-benzoyl-4,5-dihydroxy-3-nitrobenzoate |
| 1-2 | methyl 2-benzoyl-4,5-dihydroxy-3-nitrobenzoate |
| 1-3 | isopropyl 2-benzoyl-4,5-dihydroxy-3-nitrobenzoate |
| 1-4 | ethyl 2-(2-fluorobenzoyl)-4,5-dihydroxy-3-nitrobenzoate |
| 1-5 | ethyl 2-(3-fluorobenzoyl)-4,5-dihydroxy-3-nitrobenzoate |
| 1-6 | ethyl 2-(4-methylbenzoyl)-4,5-dihydroxy-3-nitrobenzoate |

TABLE 9-continued

| Compound No. | Structure |
|---|---|
| 1-7 | (4-acetylbenzoyl at position 2; nitro at 3; isopropyl ester at 1; 4,5-dihydroxy) |
| 1-8 | (4-(methoxycarbonyl)benzoyl; nitro; isopropyl ester; dihydroxy) |
| 1-9 | (2-cyanobenzoyl; nitro; isopropyl ester; dihydroxy) |
| 1-10 | (3-cyanobenzoyl; nitro; isopropyl ester; dihydroxy) |
| 1-11 | (4-cyanobenzoyl; nitro; isopropyl ester; dihydroxy) |
| 1-12 | (benzoyl; nitro; carboxylic acid; dihydroxy) |
| 1-13 | (thiophene-2-carbonyl; nitro; ethyl ester; dihydroxy) |
| 1-14 | (thiophene-3-carbonyl; nitro; ethyl ester; dihydroxy) |
| 1-15 | (isoxazole-5-carbonyl; nitro; ethyl ester; dihydroxy) |

TABLE 9-continued

| Compound No. | Structure |
|---|---|
| 1-16 | (5-methylisoxazol-3-yl)carbonyl, nitro, dihydroxy, ethyl ester benzene derivative |
| 1-17 | (isoxazol-5-yl)carbonyl, nitro, dihydroxy, isopropyl ester benzene derivative |
| 1-1 | (thiazol-2-yl)carbonyl, nitro, dihydroxy, ethyl ester benzene derivative |
| 1-19 | (thiophen-2-yl)carbonyl, nitro, dihydroxy, carboxylic acid benzene derivative |
| 1-20 | acetyl, nitro, dihydroxy, methyl ester benzene derivative |
| 1-21 | pivaloyl, nitro, dihydroxy, ethyl ester benzene derivative |
| 1-22 | pivaloyl, nitro, dihydroxy, isopropyl ester benzene derivative |
| 1-23 | trifluoroacetyl, nitro, dihydroxy, ethyl ester benzene derivative |
| 1-24 | piperidin-1-ylcarbonyl, nitro, dihydroxy, ethyl ester benzene derivative |
| 1-25 | piperidin-1-ylcarbonyl, nitro, dihydroxy, isopropyl ester benzene derivative |

TABLE 9-continued

| Compound No. | Structure |
|---|---|
| 1-26 | (2-hydroxy-3-nitro-... benzoyl phenyl ketone structure) |
| 1-27 | (4-methylphenyl ketone analog) |
| 1-28 | (phenethyl ketone analog) |
| 1-29 | (2-fluorophenyl ketone analog) |
| 1-30 | (methyl ketone analog) |
| 1-31 | (isopropyl ketone analog) |
| 1-32 | (tert-butyl ketone analog) |
| 1-33 | (cyclopentyl ketone analog) |
| 1-34 | (cyclohexyl ketone analog) |
| 1-35 | (cycloheptyl ketone analog) |

TABLE 9-continued

| Compound No. | Structure |
|---|---|
| 1-36 | 4-hydroxy-5-(tetrahydro-2H-pyran-4-carbonyl)-3-nitro-benzonitrile derivative with 3,4-dihydroxy, nitro, and cyano substituents |
| 1-37 | isoxazol-5-yl ketone with 3,4-dihydroxy-5-nitro-benzonitrile core |
| 1-38 | (5-methylisoxazol-3-yl) ketone with 3,4-dihydroxy-5-nitro-benzonitrile core |
| 1-39 | thiophen-3-yl ketone with 3,4-dihydroxy-5-nitro-benzonitrile core |
| 1-40 | thiophen-2-yl ketone with 3,4-dihydroxy-5-nitro-benzonitrile core |

TABLE 9-continued

| Compound No. | Structure |
|---|---|
| 1-41 | N,N-diethyl amide of 3,4-dihydroxy-5-nitro-benzonitrile-carboxylic acid |
| 1-42 | pyrrolidin-1-yl amide of 3,4-dihydroxy-5-nitro-benzonitrile-carboxylic acid |
| 1-43 | piperidin-1-yl amide of 3,4-dihydroxy-5-nitro-benzonitrile-carboxylic acid |
| 1-44 | azepan-1-yl amide of 3,4-dihydroxy-5-nitro-benzonitrile-carboxylic acid |
| 1-45 | morpholin-4-yl amide of 3,4-dihydroxy-5-nitro-benzonitrile-carboxylic acid |

TABLE 9-continued

| Compound No. | Structure |
|---|---|
| 1-46 | (ethyl 4-(3-cyano-5,6-dihydroxy-2-nitrobenzoyl)piperazine-1-carboxylate structure) |
| 1-47 | (methyl 2-cyano-5,6-dihydroxy-3-nitrobenzoate structure) |

The physical data of compounds 1-2 to 1-47 were shown below.

Compound 1-2
$^1$H-NMR (DMSO-$d_6$) δppm: 3.45 (3H, s), 7.45-7.51 (2H, m), 7.54 (1H, s), 7.59-7.66 (3H, m)

Compound 1-3
$^1$H-NMR (DMSO-$d_6$) δ ppm: 0.88 (6H, d, J=6.3 Hz), 4.71-4.80 (1H, m), 7.47-7.54 (2H, m), 7.58 (1H, s), 7.61-7.70 (3H, m)

Compound 1-4
$^1$H-NMR (DMSO-$d_6$) δppm: 0.99 (3H, t, J=7.1 Hz), 4.00 (2H, q, J=7.1 Hz), 7.20-7.40 (2H, m), 7.54 (1H, s), 7.60-7.80 (2H, m), 10.50-12.00 (2H, br)

Compound 1-5
$^1$H-NMR (DMSO-$d_6$) δppm: 0.96 (3H, t, J=7.1 Hz), 3.96 (2H, q, J=7.1 Hz), 7.40-7.65 (5H, m), 10.50-12.00 (2H, br)

Compound 1-6
$^1$H-NMR (DMSO-$d_6$) δppm: 0.94 (3H, t, J=7.1 Hz), 2.37 (3H, s), 3.92 (2H, q, J=7.1 Hz), 7.25-7.40 (2H, m), 7.30-7.65 (3H, m), 10.50-12.00 (2H, br)

Compound 1-7
$^1$H-NMR (DMSO-$d_6$) δ ppm: 0.92 (2H, d, J=6.3 Hz), 2.62 (3H, s), 4.72-4.84 (1H, m), 7.60 (1H, s), 7.81 (2H, d, J=8.4 Hz), 8.05 (2H, d, J=8.4 Hz)

Compound 1-8
$^1$H-NMR (DMSO-$d_6$) δ ppm: 0.90 (6H, d, J=6.3 Hz), 3.88 (3H, s), 4.50-4.90 (1H, m), 7.59 (1H, s), 7.75-7.95 (2H, m), 8.00-8.20 (2H, m), 10.50-12.00 (2H, br)

Compound 1-9
$^1$H-NMR (DMSO-$d_6$) δ ppm: 0.70-1.10 (6H, m), 4.70-4.90 (1H, m), 7.56 (1H, s), 7.60-7.90 (3H, m), 7.95-8.15 (1H, m), 10.50-12.50 (2H, br)

Compound 1-10
$^1$H-NMR (DMSO-$d_6$) δ ppm: 0.94 (6H, d, J=6.3 Hz), 4.75-4.83 (1H, m), 7.70-7.77 (1H, m), 8.00-8.17 (4H, m)

Compound 1-11
$^1$H-NMR (DMSO-$d_6$) δ ppm: 0.94 (6H, d, J=6.2 Hz), 4.73-4.83 (1H, m), 7.59 (1H, s), 7.85 (2H, d, J=8.6 Hz), 7.99 (2H, d, J=8.6 Hz), 11.38 (2H, br)

Compound 1-12
$^1$H-NMR (DMSO-$d_6$) δ ppm: 7.44-7.51 (2H, m), 7.54 (1H, s), 7.57-7.65 (3H, m)

Compound 1-13
$^1$H-NMR (DMSO-$d_6$) δppm: 0.98 (3H, t, J=7.1 Hz), 3.98 (2H, q, J=7.1 Hz), 7.10-7.25 (1H, m), 7.30-7.45 (1H, m), 7.53 (1H, s), 8.00-8.10 (1H, m), 10.50-12.00 (2H, br)

Compound 1-14
$^1$H-NMR (DMSO-$d_6$) δppm: 0.96 (3H, t, J=7.2 Hz), 3.95 (2H, q, J=7.2 Hz), 7.30-7.45 (1H, m), 7.55-7.70 (1H, m), 7.95-8.05 (1H, m), 10.50-12.00 (2H, br)

Compound 1-15
$^1$H-NMR (DMSO-$d_6$) δppm: 1.08 (3H, t, J=7.1 Hz), 4.07 (2H, q, J=7.1 Hz), 7.17 (1H, d, J=1.9 Hz), 7.58 (1H, s), 8.81 (1H, d, J=1.9 Hz), 10.50-12.50 (2H, br)

Compound 1-16
$^1$H-NMR (DMSO-$d_6$) δ ppm: 1.09 (3H, t, J=7.2 Hz), 2.40-2.60 (3H, m), 4.05 (2H, q, J=7.2 Hz), 6.65-6.75 (1H, m), 7.52 (1H, s), 10.50-12.00 (2H, br)

Compound 1-17
$^1$H-NMR (DMSO-$d_6$) δ ppm: 1.06 (6H, d, J=6.3 Hz), 4.82-4.92 (1H, m), 7.19 (1H, d, J=2.0 Hz), 7.57 (1H, s), 8.83 (1H, d, J=2.0 Hz), 11.46 (1H, br s)

Compound 1-18
$^1$H-NMR (DMSO-$d_6$) δppm: 0.98 (3H, t, J=7.0 Hz), 3.97 (2H, q, J=7.0 Hz), 7.54 (1H, s), 8.04 (1H, d, J=3.0 Hz), 8.23 (1H, d, J=3.0 Hz), 10.50-12.00 (2H, br)

Compound 1-19
$^1$H-NMR (DMSO-$d_6$) δppm: 7.15-7.22 (1H, m), 7.50-7.56 (1H, m), 7.70 (1H, s), 8.06-8.12 (1H, m)

Compound 1-20
$^1$H-NMR (DMSO-$d_6$) δ ppm: 2.41 (3H, s), 3.82 (3H, s), 7.52 (1H, s), 11.16 (1H, br. s.)

Compound 1-21
$^1$H-NMR (DMSO-$d_6$) δ ppm: 1.08 (9H, s), 1.28 (3H, t, J=7.1 Hz), 4.10-4.40 (2H, m), 7.53 (1H, s), 10.60-12.00 (2H, br)

Compound 1-22
$^1$H-NMR (DMSO-$d_6$) δ ppm: 1.08 (9H, s), 1.29 (6H, d, J=6.3 Hz), 4.99-5.08 (1H, m), 7.50 (1H, s), 11.16 (2H, br s)

Compound 1-23
$^1$H-NMR (DMSO-$d_6$) δ ppm: 1.29 (3H, t, J=7.1 Hz), 4.32 (2H, q, J=7.1 Hz), 7.54 (1H, s)

Compound 1-24
$^1$H-NMR (DMSO-$d_6$) δ ppm: 1.25 (3H, t, J=7.0 Hz), 1.34-1.65 (6H, m), 2.93-3.25 (3H, m), 3.66-3.72 (1H, m), 4.22 (2H, q, J=7.0 Hz), 7.52 (1H, s), 11.07 (2H, br s)

Compound 1-25
$^1$H-NMR (DMSO-$d_6$) δ ppm: 1.21-1.27 (6H, m), 1.32-1.68 (6H, m), 2.90-3.17 (3H, m), 3.77-3.83 (1H, m), 4.98-5.08 (1H, m), 7.51 (1H, s), 11.04 (2H, br s)

Compound 1-26
$^1$H-NMR (DMSO-$d_6$) δ ppm: 7.33 (1H, s), 7.50-7.65 (2H, m), 7.65-7.85 (3H, m)

Compound 1-27
$^1$H-NMR (DMSO-$d_6$) δ ppm: 2.41 (3H, s), 7.29-7.42 (3H, m), 7.67 (2H, d, J=8.3 Hz)

Compound 1-28
$^1$H-NMR (DMSO-$d_6$) δ ppm: 2.89-2.92 (2H, m), 3.16-3.20 (2H, m), 7.13-7.30 (6H, m)

Compound 1-29
$^1$H-NMR (DMSO-$d_6$) δ ppm: 7.29 (1H, s), 7.36-7.40 (2H, m), 7.70-7.80 (2H, m)

Compound 1-30
$^1$H-NMR (DMSO-$d_6$) δ ppm: 2.55 (3H, s), 7.27 (1H, s)

Compound 1-31
 ¹H-NMR (DMSO-d$_6$) δ ppm: 1.09 (6H, d, J=7.1 Hz), 2.95-3.15 (1H, m), 7.27 (1H, s)
Compound 1-32
 ¹H-NMR (DMSO-d$_6$) δ ppm: 1.16 (9H, s), 7.28 (1H, s)
Compound 1-33
 ¹H-NMR (DMSO-d$_6$) δ ppm: 1.45-1.95 (8H, m), 3.25-3.45 (1H, m), 7.28 (1H, s)
Compound 1-34
 ¹H-NMR (DMSO-d$_6$) δ ppm: 1.09-1.86 (10H, m), 2.74-2.86 (1H, m), 7.30 (1H, s)
Compound 1-35
 ¹H-NMR (DMSO-d$_6$) δ ppm: 1.48-1.77 (5H, m), 3.02-3.14 (2H, m), 3.28-3.37 (2H, m), 3.83-3.91 (2H, m), 7.26 (1H, s)
Compound 1-36
 ¹H-NMR (DMSO-d$_6$) δ ppm: 1.34-1.71 (6H, m), 1.79-1.90 (2H, m), 2.94-3.06 (1H, m), 7.29 (1H, s)
Compound 1-37
 ¹H-NMR (DMSO-d$_6$) δppm: 7.30 (1H, s), 7.42 (1H, d, J=2.0 Hz), 8.91 (1H, d, J=2.0 Hz)
Compound 1-38
 ¹H-NMR (DMSO-d$_6$) δ ppm: 2.40-2.60 (3H, m), 6.80-6.90 (1H, m), 7.31 (1H, s)
Compound 1-39
 ¹H-NMR (DMSO-d$_6$) δ ppm: 7.31 (1H, s), 7.45-7.55 (1H, m), 7.65-7.80 (1H, m), 8.30-8.40 (1H, m)
Compound 1-40
 ¹H-NMR (DMSO-d$_6$) δ ppm: 7.20-7.35 (2H, m), 7.60-7.70 (1H, m), 8.15-8.30 (1H, m)
Compound 1-41
 ¹H-NMR (DMSO-d$_6$) δ ppm: 1.07-1.12 (6H, m), 3.18-3.50 (4H, m), 7.28 (1H, s), 11.41 (1H, br s)
Compound 1-42
 ¹H-NMR (DMSO-d$_6$) δ ppm: 1.81-1.93 (4H, m), 3.21-3.46 (4H, m), 7.28 (1H, s), 11.37 (1H, br s)
Compound 1-43
 ¹H-NMR (DMSO-d$_6$) δ ppm: 1.46-1.64 (6H, m), 7.27 (1H, s)
Compound 1-44
 ¹H-NMR (DMSO-d$_6$) δ ppm: 1.52-1.70 (8H, m), 3.24-3.57 (4H, m), 7.28 (1H, s), 11.36 (1H, br s)
Compound 1-45
 ¹H-NMR (DMSO-d$_6$) δ ppm: 3.25-3.67 (8H, m), 7.28 (1H, s)
Compound 1-46
 ¹H-NMR (DMSO-d$_6$) δ ppm: 1.19 (3H, t, J=7.0 Hz), 3.28-3.67 (8H, m), 4.07 (2H, q, J=7.0 Hz), 7.27 (1H, s)
Compound 1-47
 ¹H-NMR (DMSO-d$_6$) δ ppm: 3.82 (3H, s), 7.28 (1H, s)

Example 2-1

5-Ethoxycarbonyloxy-2-(2-fluorobenzoyl)-4-hydroxy-3-nitro-benzonitrile (compound 2-1)

A mixture of 2-(2-fluorobenzoyl)-4,5-dihydroxy-3-nitrobenzonitrile (compound 1-29) (70 mg), ethyl chloro-carbonate (30 mg) and N,N-dimethylforamide (1 mL) was stirred at 50° C. for 3 hours. Water and ethyl acetate were added to the mixture. The organic layer was washed with water, and dried over anhydrous magnesium sulfate, and concentrated under reduced pressure. The residue was purified by silica gel column chromatography (eluent: 50-100% ethyl acetate/hexane, gradient elution) to give the title compound (60 mg). The structural formula was illustrated in table 10.
 ¹H-NMR (CDCl$_3$) δppm: 1.42 (3H, t, J=7.0 Hz), 4.38 (2H, q, J=7.0 Hz), 7.06-7.16 (1H, m), 7.35-7.44 (1H, m), 7.62-7.71 (1H, m), 7.78 (1H, s), 8.13-8.21 (1H, m), 11.18 (1H, br)

Compounds 2-2 to 2-4 were prepared in a manner similar to those as described in example 2-1 using the corresponding nitrocatechol instead of 2-(2-fluorobenzoyl)-4,5-dihydroxy-3-nitrobenzonitrile. These were illustrated in table 10.

The physical data of compounds 2-2 to 2-4 were shown below.
Compound 2-2
 ¹H-NMR (CDCl$_3$) δ ppm: 1.39-1.45 (3H, m), 1.50-1.83 (6H, m), 3.16-3.36 (2H, m), 3.70-3.90 (2H, m), 4.33-4.44 (2H, m), 7.63-7.75 (1H, m)
Compound 2-3
 ¹H-NMR (CDCl$_3$) δ ppm: 1.24 (3H, t, J=7.2 Hz), 1.42 (3H, t, J=7.2 Hz), 4.20-4.28 (2H, m), 4.38 (2H, q, J=7.1 Hz), 7.11 (1H, d, J=2.0 Hz), 8.22 (1H, s), 8.41 (1H, d, J=1.9 Hz)
Compound 2-4
 ¹H-NMR (CDCl$_3$) δ ppm: 1.42 (9H, s), 7.10 (1H, ddd, J=11.3, 8.5, 1.0 Hz), 7.36-7.41 (1H, m), 7.63-7.69 (2H, m), 8.17 (1H, dt, J=7.7, 1.8 Hz), 11.13 (1H, br)

Compound 3-1

4,5-Bis(ethoxycarbonyloxy)-2-(2-fluorobenzoyl)-3-nitro-benzonitrile (compound 3-1)

To a mixture of 2-(2-fluorobenzoyl)-4,5-dihydroxy-3-nitrobenzonitrile (compound 1-29) (70 mg) and tetrahydrofuran (2.0 mL) were added ethyl chlorocarbonate (70 μl) and triethylamine (110 μl) under ice-bath cooling. After stirring for 30 minutes, the mixture was stirred at room temperature for 2 days. The mixture was diluted with ethyl acetate, and washed with 1 mol/L hydrochloric acid and brine, dried over anhydrous magnesium sulfate, and concentrated under reduced pressure. The residue was purified by silica gel column chromatography (eluent: 0%-30% ethyl acetate/hexane, gradient elution) to give the title compound (103 mg). The structural formula was illustrated in table 10.
 ¹H-NMR (CDCl$_3$) δ ppm: 1.41 (3H, t, J=7.1 Hz), 1.43 (3H, t, J=7.1 Hz), 4.40 (2H, q, J=7.1 Hz), 4.41 (2H, q, J=7.1 Hz), 7.15 (1H, ddd, J=11.0, 8.4, 0.9 Hz), 7.35-7.39 (1H, m), 7.65-7.71 (1H, m), 7.98 (1H, s), 8.04 (1H, dt, J=7.6, 1.6 Hz)

Compound 3-2

Ethyl 4,5-bis(diethylcarbamoyloxy)-3-nitro-2-(piperidine-1-carbonyl)benzoate (compound 3-2)

The title compound was prepared in a manner similar to those as described in example 3-1 using diethylcarbamoyl chloride instead of ethyl chlorocarbonate. The structural formula was illustrated in table 10.
 ¹H-NMR (CDCl$_3$) δ ppm: 1.16-1.25 (12H, m), 1.36 (6H, t, J=7.2 Hz), 1.45-1.79 (6H, m), 3.05-3.15 (1H, m), 3.20-3.50 (10H, m), 3.85-3.95 (1H, m), 4.30-4.40 (2H, m), 8.09 (1H, s)

TABLE 10

| Compound No. | Structure |
|---|---|
| 2-1 | (structure) |
| 2-2 | (structure) |
| 2-3 | (structure) |
| 2-4 | (structure) |

TABLE 10-continued

| Compound No. | Structure |
|---|---|
| 3-1 | (structure) |
| 3-2 | (structure) |

Test Example 1

Human COMT Inhibitory Potency

1) Preparation of Recombinant Human COMT
(1) Preparation of Recombinant Human Catechol-O-Methyl Transferase According to the DNA sequence of NCBI (National Center for Biotechnology Information) accession number (BC011935), two oligonucleotide primers were designed to amplify the target DNA sequence coding full-length human catechol-O-methyl transferase (hereinafter referred to as "COMT") as shown in Sequence ID No. 1. Sequences of the 5'-primer and the 3'-primer were indicated in Sequence ID No. 3 and 4, respectively. For ease in insertion of corresponding PCR product into the desired vector, these primers includes restriction enzyme sites of BamH I and EcoR I on the 5'-side and the 3'-side, respectively.

Each of the 5'-primer indicated in Sequence ID No. 3 and the 3'-primer indicated in Sequence ID NO.4 was diluted with TE buffer to prepare 15 pmol/μL solutions. A mixture for PCR reaction was prepared with $H_2O$ (for PCR, 34.8 μL), 25 mmol/L $MgSO_4$ (2.0 μL), 2 mmol/L dNTPs (5.0 μL) and 10-fold concentrated buffer for KOD plus DNA Polymerase (5.0 μL, TOYOBO). After the addition of each primer pairs (1 μL, 15 pmol) following human liver cDNA (5.0 μL, Clontech), 1.0 μL KOD plus (TOYOBO) was added to the above reaction mixture. Thereafter, PCR reaction was executed as referred to hereinafter; after the procedure at 94° C. for 2 minutes, PCR reactions were carried out for 40 cycles, each consisting of 94° C. for 15 seconds, 59° C. for 30 seconds, and 68° C. for 1 minutes and then terminated at 68° C. for 5 minutes and at 4° C. for 10 minutes.

PCR product was purified using a QIAquick PCR Purification Kit (QIAGEN) and the desired DNA insert was eluted using EB buffer (30 μL) included in the corresponding kit.

(2) Double Digestion of Recombinant Human COMT DNA Insert and pGEX-2T Vector

The obtained recombinant human COMT DNA insert (1.5 μg) was mixed with 10-fold concentrated EcoR I buffer (3.0 μL, New England Biolab), $H_2O$ (11.1 μL), BamH I (1.5 μL, 15 U, 10 U/μL) and EcoR I (1.0 μL, 15 U, 10 U/μL) and then incubated at 37° C. for 1.5 hours. Thereafter 10-fold concentrated loading buffer was added to the mixture. Following the purification on an electrophoresis, a piece of the gel region including objective digested fragment was removed and purified with a MinElute Gel Extraction Kit (QIAGEN). Double digestion and purification of pGEX-2T vector DNA (1.5 μg, Amersham) was also performed in a similar way as described above.

(3) Ligation and E. coli JM109 transformation

Double-digested DNA of pGEX-2T vector (2.0 μL, 50 ng) and insert DNA (1.24 μL, 33.4 ng) were added to 2-fold concentrated ligation buffer (3.24 μL, Promega) and mixed. The mixture was incubated at 25° C. for 1 hour following the addition of T4 ligase (1.0 μL, 3 U/μL, Promega). This solution of ligase-treated mixture (5 μL) was transferred to E. coli JM109 (100 μL) thawed at 0° C., and was gently mixed and incubated at 0° C. for 30 minutes. The mixture was heat-shocked at 42° C. for 40 seconds, without excessive shaking, followed by cooling at 0° C. for 10 minutes. After heat shock step, SOC medium (450 μL) was added and the mixture was shaken at 37° C. for 1 hour. Each aliquot (50 μL and 200 μL) of the mixture was subsequently seeded onto LB plates (a diameter of 9 cm, ampicillin 100 μg/mL) and statically cultured at 37° C. for 16 hours. As a result, colonies were observed on the plates.

(4) Colony Selection of JM109 Transformed with GST-Fusion Recombinant Human COMT Plasmid Some colonies were selected from above-mentioned statically cultured plates and each colony was inoculated into 2 mL of LB-ampicillin (100 μg/mL) liquid medium using sterile picks. After the shaking culture at 37° C. for 16 hours, aliquots (200 μL) of each culture were removed into 1.5 mL microtubes and plasmids were extracted by a phenol extraction. The obtained plasmids were resolubilized in TE buffer and separated by electrophoresis. Primary positive colonies were identified according to the electrophoretic mobilities of their extracted plasmids similar to that of pGEX-2T vector without insert DNA and reconfirmed by double digestion using restriction enzymes as follows.

DNA solutions (7 μL) prepared from primary positive colonies indicated above were mixed with 10-fold concentrated EcoR I buffer (0.9 μL, New England Biolab), then BamH I (0.5 μL, 10 U/μL) and EcoR I (0.5 μL, 15 U/μL) were added to the mixture. The solution was analyzed by electrophoresis after warming (37° C., 1 hour). Secondary positive colonies were identified as those with a band of about 670 bp.

(5) Extraction and Purification of GST-Fusion Recombinant Human COMT Plasmid from E. Coli JM109

An aliquot (100 μL) from the culture of E. coli JM109 transformed with GST-fusion recombinant human COMT plasmid, which determined as a secondary positive colony at (4), was stored as a glycerol stock, whereas the rest was centrifuged at 12,000 rpm for 10 minutes to obtain E. coli pellet. Plasmid DNA was purified from the E. coli pellet by QIAGEN Plasmid mini kit (QIAGEN) and its concentration was determined by OD 260 nm (247 ng/μL). DNA sequence analysis according to a conventional method confirmed that the DNA sequence indicated in Sequence ID No. 2 was properly inserted at the desired site.

(6) Transformation of Competent E. Coli BL21 (DE3) Codon Plus RP by GST-Fusion Recombinant Human COMT Plasmid DNA For transformation and plate culture in the same fashion as (3), 1 μL of purified GST-fusion recombinant human COMT plasmid DNA (1 ng/μL) with valid sequence indicated in (5) was added to 50 μL of cell suspension of competent E. Coli BL21 (DE3) CODON PLUS RP thawed at 0° C.

(7) Expression of GST-Fusion Recombinant Human COMT

A colony was picked up from the plate with transformed E. Coli BL21 (DE3) CODON PLUS RP and cultured with shaking at 37° C. for 15 hours in 5 mL of LB-ampicillin (100 μg/mL) liquid medium. An aliquot of culture medium (50 μL) was stored at −80° C. as a glycerol stock. A piece of the glycerol stock was used to inoculate into 150 mL of LB-ampicillin (100 μg/mL) medium and cultured with shaking at 37° C. for 16 hours. The culture was diluted into 7 culture flasks with LB-ampicillin (100 μg/mL) medium (500 mL each), and then each culture was grown at 20° C. for 4.5 hours with shaking to a cell density of OD 600 nm=0.44, at which point 50 μL of isopropyl-β-D-thiogalactopyranoside (1 mol/L) was added to each culture. After that, each culture was incubated under the same conditions for an additional 18 hours. E. coli pellet was harvested by centrifugation for 20 minutes at 9,000 rpm, divided into four equal portions (4 g) and stored at −80° C. until use.

(8) Thrombin Processing of GST-Fusion Recombinant Human COMT

E. coli pellet obtained in (7) was suspended in BugBuster Reagent (Novagen, 40 mL) containing Bensonase (Novagen, 30 μL) and rLysozyme (Novagen, 1 μL) and the E. coli was treated with a gentle rotation at room temperature for 15 minutes. The obtained cell lysate was separated by centrifugation at 12,000 rpm for 20 minutes at 4° C. and the supernatant was recovered. This supernatant was incubated at 4° C. for 1 hour on a rotating platform with a 20 mL of a 50% slurry of Glutathione Sepharose 4B (resin-bed volume of 10 mL), which was previously equilibrated with D-PBS (Dulbecco's phosphate-buffered saline). The resultant resin was separated on a filter from the filtrate and washed five times with 30 mL of D-PBS, followed by three additional washing steps with 30 mL of thrombin processing buffer (150 mmol/L NaCl, 50 mmol/L Tris-HCl pH8.0, 10% glycelol, 2.5 mmol/L $CaCl_2$, and 0.5% n-octyl-β-D-glucopyranoside). After the last wash, the resin was again suspended with thrombin processing buffer at a final volume of 30 mL. Thirty units of thrombin protease (Amersham Biosciences) was added to the resin suspension, and thrombin processing was allowed to proceed with a gentle rotation for 15 hours at 4° C. The resin suspension was filtrated and recombinant human COMT solution obtained as a filtrate was stored at −80° C. until assayed.

2) Measurement of Human COMT Inhibitory Potency

Measurement of human COMT inhibitory potency was performed according to the method of G. Zürcher et al (J. Neurochem., 1982, vol. 38, p. 191-195) with a minor modification. Aliquot (0.25 μL) of recombinant human COMT prepared in 1) (approximately 1 mg/mL) was preincubated with a test compound for 5 minutes at 37° C. in the reaction mixture, composed of 40 μL potassium phosphate buffer (500 mmol/L, pH7.6), 10 μL magnesium chloride (100 mmol/L), 10 μL dithiothreitol (62.5 mmol/L) and 0.5 adenosine deaminase (2550 units/mL). Control samples were prepared in the same way, but the test compounds were replaced with an equal volume (5 μL) of dimethyl sulfoxide. After the addition of 20 μL [$^3$H]-S-adenosyl-L-methionine (12.5 mmol/L, 1.2

Ci/mol; Amersham Biosciences), the reaction was started by the addition of 25 μL catechol substrate (7 mmol/L). The reaction mixture, final volume 0.25 mL, was incubated at 37° C. for 30 minutes. The reaction was then stopped by the addition of 0.25 mL of ice-cold 1 mol/L hydrochloric acid containing 0.1 g/L guaiacol. After the addition of 2.5 mL scintillator OPTI-FLUOR (registered mark) 0 (Packerd), and following 1-minute vigorous shaking, the radioactivity present in the organic phase was then directly counted in a liquid scintillation counter (Packard; TRICARB 1900CA). Blanks were incubated without catechol substrate (substrate was added after the termination of reaction). The $IC_{50}$ value indicates the molar concentration required to inhibit 50% of the enzyme activity. As comparative examples, tolcapone; entacapone; (3,4-dihydroxy-2-nitrophenyl)phenymethanone (comparative example 1), (6-benzoyl-3,4-dihydroxy-2-nitrophenyl)phenylmethanone (comparative example 2) and carbonic acid 4,5-dibenzoyl-2-ethoxycarbonyloxy-3-nitro-phenyl ester ethy ester (comparative example 3), which are described in the patent literature 3, were assayed in the similar fashion. These results were shown in Table 11.

TABLE 11

| Compound No. | $IC_{50}$ (nmol/L) |
| --- | --- |
| 1-1 | 7.8 |
| 1-2 | 8.9 |
| 1-7 | 4.0 |
| 1-8 | 8.3 |
| 1-9 | 7.0 |
| 1-13 | 8.4 |
| 1-15 | 7.1 |
| 1-18 | 4.7 |
| 1-20 | 9.5 |
| 1-23 | 8.1 |
| 1-27 | 9.7 |
| 1-29 | 6.8 |
| 1-34 | 8.1 |
| 1-37 | 8.6 |
| 1-38 | 8.6 |
| Tolcapone | 9.0 |
| Entacapone | 11.1 |
| Comparative example 1 | 40.4 |
| Comparative example 2 | 54.0 |
| Comparative example 3 | 1180 |

Test Example 2

Inhibition of Rat Brain and Liver COMT Activity by COMT Inhibitors

1) Administration and Sampling 7-week-old male Sprague-Dawley rats weighing 200 g to 250 g (Charles River Laboratories Japan Inc.) were fasted for 16 hours. All test compounds were dissolved in dimethylsulfoxide/polyethylene glycol 400/0.1 mol/L aqueous solution of arginine=0.5/20/79.5 (2 mg/mL) immediately before the oral administration. 1 hour and 5 hours after the test compound administration (10 mg/kg), animals were sacrificed by decapitation and brain and liver were isolated for COMT activity measurement. Tissue samples for control were harvested from untreated animal. All tissues were immediately frozen in liquid nitrogen. Frozen tissues were homogenized in 4-fold volume (w/v) of ice-cold homogenization buffer (Dulbecco's phosphate-buffered saline supplemented with 0.5 mmol/L dithiothreitol). Homogenates were centrifuged (4° C.) for 10 minutes at 900×g (Kubota Co., Ltd., High-capacity refrigerated centrifuge 8800). Supernatant fraction containing both S—COMT (soluble COMT) and MB-COMT (membrane-bound COMT), namely total COMT fraction, was stored at −80° C. until measurement. Protein concentrations of the respective samples were determined using BCA protein assay (Pierce).

2) Measurement of COMT Activity

COMT assay was performed according to the method of G. Zürcher et al (J. Neurochem., 1982, vol. 38, p. 191-195) with a minor modification. Aliquots (approximately 50 mL and 3.5 mL for brain and liver, respectively) of homogenate preparations (protein concentrations of the preparations were approximately 15 mg/mL and 35 mg/mL, respectively) was preincubated for 5 minutes at 37° C. in the reaction mixture, composed of 40 mL potassium phosphate buffer (500 mmol/L, pH 7.6), 10 mL magnesium chloride (100 mmol/L), 10 mL dithiothreitol (62.5 mmol/L) and 0.5 mL adenosine deaminase (2550 units/mL). After the addition of 20 mL [$^3$H]-S-adenosyl-L-methionine (12.5 mmol/L, 44.4 GBq/mol; Amersham Biosciences), the reaction was started by the addition of 25 mL catechol substrate (7 mmol/L). The reaction mixture, final volume 0.25 mL, was incubated at 37° C. for 90 minutes (brain) or 30 minutes (liver). The reaction was then stopped by the addition of 0.25 mL of ice-cold 1 mol/L hydrochloric acid containing 0.1 g/L guaiacol. After the addition of 2.5 mL scintillator OPTI-FLUOR (registered mark) 0 (Packerd), and following 1-minute vigorous shaking, the radioactivity present in the organic phase was then directly counted in a liquid scintillation counter (Packard; TRICARB 1900CA). Control samples were incubated without catechol substrate (substrate was added after the termination of reaction). COMT activity % was shown as a percentage of the Control sample (100%). As comparative examples, tolcapone and entacapone were assayed in the similar fashion. These results were shown in Table 12.

TABLE 12

| Compound No. | Brain (COMT activity %) | | Liver (COMT activity %) | |
| --- | --- | --- | --- | --- |
| | 1 hour | 5 hours | 1 hour | 5 hours |
| 1-1 | 8.9 | 56.2 | 0.6 | 9.0 |
| 1-13 | 14.8 | 61.0 | 6.6 | 15.3 |
| 1-34 | 62.2 | 78.7 | 0.0 | 1.0 |
| tolcapone | 9.9 | 57.9 | 2.5 | 30.0 |
| entacapone | 85.3 | 107.6 | 15.63 | 78.4 |

These results demonstrated that the compounds of the present invention exhibited more persistent and potent inhibitory action on liver COMT than tolcapone and entacapone.

Test Example 3

Rat Hepatocyte Toxicities

After rat cryopreserved hepatocytes $3 \times 10^{-6}$ cells/vial, stored at −150° C., was warmed at 37° C., and the hepatocytes were added into a thawing medium with glucose (10 mL) and agitated. The suspension was centrifuged at 1000 rpm for 1 minute. After the supernatant was removed, the cell pellet was suspended in Williams E medium (15 mL). A solution of drug in dimethyl sulfoxide was prepared at 45, 15, 4.5, 1.5, 0.45 mmol/L, then each of the drug solutions and dimethyl sulfoxide as a control was dispensed by 2.0 μL to a test tube. The above cell suspension (300 μL) was dispensed into the tube and re-suspended. Every 100 μL of each suspension was dispensed to a 96 well-plate, and the plate was incubated for 4 hours at 37° C. in $CO_2$ incubators. According to Cell viability assay provided from Promega Corporation, ATP activity was measured. The EC50 value indicates the concentration that shows 50% of the number of viable cells of control. These results were shown in Table 13.

TABLE 13

| Compound No. | $EC_{50}$ (μmol/L) |
|---|---|
| 1-1 | 262 |
| 1-2 | >300 |
| 1-13 | >300 |
| 1-20 | >300 |
| 1-27 | >300 |
| 1-34 | >300 |
| 1-38 | >300 |
| 1-43 | >300 |
| Tolcapone | 34.3 |
| Entacapone | 111 |

These results suggest that the compounds of the present invention exhibited extremely minor hepatocyte toxicities as compared with tolcapone or entacapone.

Test Example 4

The Potentiation on the Effecacy of L-Dopa in Unilateral 6-Hydroxydopamine-Lesioned Hemi-Parkinsonian Rats (1) Drugs The following compounds were used: 6-hydroxydopamine hydrochloride (6-OHDA, Sigma); desipramine hydrochloride (desipramine, Sigma); L-ascorbic acid (Sigma); sodium pentobarbital (Nembutal inj., Dainippon Sumitomo Pharma Co., Ltd.); apomorphine hydrochloride hemihydrate (apomorphine, Sigma); 3,4-dihydroxyphenylalanine (L-dopa, Sigma); carbidopa monohydrate (carbidopa, Kemprotec Ltd.); 0.5% methylcellulose (Wako Pure Chemicals).

6-OHDA was dissolved at 2 mg/ml in a saline solution containing 0.2% L-ascorbic acid. Desipramine was dissolved at 10 mg/mL in distilled water in a hot-water bath. Apomorphine was dissolved at 0.1 mg/mL in a saline solution. L-dopa/carbidopa was suspended in a 0.5% methylcellulose solution. Test compounds were dissolved in a solution containing 0.5% dimethylsulfoxide, 20% polyethylene glycol and 79.5% of a 0.1 mol/L aqueous solution of arginine.

(2) Preparation of 6-OHDA-Lesioned Model

Preparation of 6-OHDA-lesioned model was performed according to the method of nonpatent literature 6 with a minor modification. Male Sprague-Dawley rats (6-weeks-old, Charles River Laboratories Japan Inc.) were anaesthetized with intraperitoneal sodium pentobarbital (45 mg/kg) administration and placed in a stereotaxic frame (Narishige, Tokyo, Japan). In order to prevent 6-OHDA-induced damage of noradrenergic neurons, intraperitoneal desipramine injection (25 mg/kg) was given 30 minutes before the 6-OHDA injection. After the bregma identification via a middle calvarial incision, the skull was drilled using a dental drill at the site of 6-OHDA injection. The lesion was made by injecting 6-OHDA (8 μg in 4 μL at a speed of 1 μL/minute) unilaterally into the left medial forebrain bundle (the lesion coordinates; A/P −2.5 mm, L/M −1.8 mm, and V/D −8.0 mm, from the bregma point and surface of the skull) by using a injection cannula (30 gauge needle) connected to a microsyringe (Hamilton). The cannula was carefully removed from the animal after keeping placed on the lesion site for 5 minutes. The skull was filled its hole with dental cement, disinfected, and the scalp incision was surgically sutured. Animals recovered from anesthesia were housed as usual until the day of the experiment.

(3) Evaluation of Turning Behavior

Three weeks after the lesion, rats were tested on the basis of their contralateral rotation (single rotation was defined as a 360° turn) in response to 0.1 mg/kg apomorphine given subcutaneously. For behavioral observation, rats were placed in plastic cylinders of radius 20 cm and turning behavior was videotaped and quantified by rat-rotation auto counting system R-RACS (Kissei Wellcom Co., Ltd.). Animals that turned over 100 rotation counts during 1 hour were accepted for further experiments. On the experimental day, animals were fasted overnight, and all test compounds were orally given at doses of 10 mg/kg with concomitant oral administration of 5 mg/kg L-dopa and 30 mg/kg carbidopa. After the drug administration, the numbers of contralateral rotation were measured. The onset and the offset of the action were each the time rat rotated over 10 counts per 10-minute period and rotated less than 10 counts per 10-minute period for more than 60 minutes, respectively. The duration of the action and total counts were employed to express the drug potency. The duration of the action was defined as the subtraction from the time just before the time less than 10 rotation counts for more than 60 minutes to those over 10 rotation counts in a 10-minute period. Total counts were defined as the summation of the rotation counts in a 10-minute period during the drug action. Total counts and the duration of the response were listed in Table 14. Similarly, the result of the control group that was treated only with L-dopa and carbidopa was shown in the same table.

TABLE 14

| Compound No. | Duration (minutes) | Total counts |
|---|---|---|
| Control | 184.3 | 981.0 |
| 1-1 | 522.5 | 3188.3 |
| 1-2 | 452.9 | 3569.0 |
| 1-13 | 461.4 | 3395.7 |
| Entacapone | 271.4 | 1606.6 |
| Tolcapone | 430.0 | 2578.7 |

From these results, as compared with control animals which were treated only with L-dopa/carbidopa, remarkable potentiation of drug effects were observed in animals administered with compounds of the present invention in combination with L-dopa/carbidopa.

INDUSTRIAL APPLICABILITY

Compounds of the present invention exhibit potent COMT inhibitory activities, and are accordingly useful for treating or preventing Parkinson's disease, depression or hypertension. Especially, compounds of the present invention are useful for treating or preventing Parkinson's disease since use of compounds of the present invention in combination with L-dopa increases bioavailability of L-dopa remarkably.

SEQUENCE LISTING FREE TEXT

[SEQ ID No. 1]
Sequence ID No. 1 indicates the sequence of recombinant human catechol-O-methyl transferase.

[SEQ ID No. 2]
Sequence ID No. 2 indicates the DNA sequence, which was intended to express the recombinant human catechol-O-methyl transferase shown in sequence ID No. 1, amplified by using primer pair shown in sequence ID No. 3 and 4.

[SEQ ID No. 3]
Sequence ID No. 3 indicates the sequence of 5'-primer employed to amplify the DNA sequence shown in sequence ID No. 2.

[SEQ ID No. 4]
SEQ ID No. 4 indicates the sequence of 3'-primer employed to amplify the DNA sequence shown in sequence ID No. 2.

The invention claimed is:

1. A compound represented by general formula (I):

$$\text{(I)}$$

or a pharmaceutically acceptable salt thereof,
wherein
$R^1$ and $R^2$ are each independently a hydrogen atom, a lower acyl group, a lower alkoxycarbonyl group or —C(O)NR$^{11}$R$^{12}$, or $R^1$ and $R^2$ are joined together to form —C(O)—;

$R^3$ is:
a) a lower alkyl group,
b) a halo-lower alkyl group,
c) a cycloalkyl group,
d) a hydroxycycloalkyl group,
e) a heterocycloalkyl group,
f) an aryl group, wherein the ring of the aryl group is unsubstituted or substituted with 1 to 5 substituents independently selected from the group consisting of a halogen atom, a lower alkyl group, a halo-lower alkyl group, a cyano group, a lower acyl group, a lower alkoxy group, a hydroxy group and a lower alkoxycarbonyl group,
g) a heteroaryl group, wherein the ring of the heteroaryl group is unsubstituted or substituted with 1 to 3 substituents independently selected from the group consisting of a halogen atom, a lower alkyl group, a halo-lower alkyl group, a lower alkoxy group and a hydroxy group,
h) an aralkyl group, wherein the ring of the aralkyl group is unsubstituted or substituted with 1 to 5 substituents independently selected from the group consisting of a halogen atom, a lower alkyl group, a halo-lower alkyl group and a lower alkoxy group,
i) a lower alkoxy group,
j) a halo-lower alkoxy group,
k) a lower alkoxy-lower alkoxy group,
l) a cycloalkyloxy group, or
m) —NR$^{11}$R$^{12}$;

$R^4$ is:
a) a cyano group,
b) a lower alkoxycarbonyl group,
c) a halo-lower alkoxycarbonyl group,
d) a lower alkoxy-lower alkoxycarbonyl group,
e) a cycloalkyloxycarbonyl group, or
f) a carboxy group;

$R^{11}$ and $R^{12}$ are each independently a hydrogen atom, a lower alkyl group, a cycloalkyl group, a phenyl group or an aralkyl group, or $R^{11}$ and $R^{12}$, together with the nitrogen atom to which they are bonded, form a cyclic amino group.

2. The compound according to claim 1, or a pharmaceutically acceptable salt thereof, wherein $R^1$ and $R^2$ are a hydrogen atom.

3. The compound according to claim 2, or a pharmaceutically acceptable salt thereof, wherein $R^3$ is:
   a) a lower alkyl group,
   b) a halo-lower alkyl group,
   c) a cycloalkyl group,
   d) a heterocycloalkyl group,
   e) an aryl group, wherein the ring of the aryl group is unsubstituted or substituted with 1 to 5 substituents independently selected from the group consisting of a halogen atom, a lower alkyl group, a halo-lower alkyl group, a cyano group, a lower acyl group, a lower alkoxy group and a lower alkoxycarbonyl group,
   f) a heteroaryl group, wherein the ring of the heteroaryl group is unsubstituted or substituted with 1 to 3 substituents independently selected from the group consisting of a halogen atom, a lower alkyl group, a halo-lower alkyl group and a lower alkoxy group,
   g) an aralkyl group, wherein the ring of the aralkyl group is unsubstituted or substituted with 1 to 5 substituents independently selected from the group consisting of a halogen atom, a lower alkyl group, a halo-lower alkyl group and a lower alkoxy group,
   h) a lower alkoxy group, or
   i) —$NR^{11}R^{12}$.

4. The compound according to claim 3, or a pharmaceutically acceptable salt thereof, wherein $R^4$ is:
   a) a cyano group,
   b) a lower alkoxycarbonyl group, or
   c) a carboxy group.

5. The compound according to claim 4, or a pharmaceutically acceptable salt thereof, wherein $R^3$ is:
   a) a cycloalkyl group,
   b) an aryl group, wherein the ring of the aryl group is unsubstituted or substituted with 1 to 5 substituents independently selected from the group consisting of a halogen atom, a lower alkyl group, a halo-lower alkyl group, a cyano group, a lower acyl group, a lower alkoxy group and a lower alkoxycarbonyl group, or
   c) a heteroaryl group, wherein the ring of the heteroaryl group is unsubstituted or substituted with 1 to 3 substituents independently selected from the group consisting of a halogen atom, a lower alkyl group, a halo-lower alkyl group and a lower alkoxy group.

6. A compound, or a pharmaceutically acceptable salt thereof, selected from the group consisting of:
   ethyl 2-benzoyl-4,5-dihydroxy-3-nitrobenzoate;
   methyl 2-benzoyl-4,5-dihydroxy-3-nitrobenzoate;
   ethyl 4,5-dihydroxy-3-nitro-2-(thiophen-2-carbonyl)-benzoate;
   4,5-dihydroxy-2-(4-methylbenzoyl)-3-nitrobenzonitrile;
   2-cyclohexanecarbonyl-4,5-dihydroxy-3-nitrobenzo-nitrile;
   ethyl 4,5-dihydroxy-2-(isoxazole-5-carbonyl)-3-nitrobenzoate;
   isopropyl 4,5-dihydroxy-2-(isoxazole-5-carbonyl)-3-nitrobenzoate;
   ethyl 4,5-dihydroxy-3-nitro-2-(thiazole-2-carbonyl)-benzoate; and
   4,5-dihydroxy-2-isobutyryl-3-nitrobenzonitrile.

7. A pharmaceutical composition which comprises, as an active ingredient, a compound according to claim 1 or a pharmaceutically acceptable salt thereof.

8. A pharmaceutical composition comprising a compound according to claim 1 or a pharmaceutically acceptable salt thereof and at least one selected from L-dopa or an aromatic L-amino acid decarboxylase inhibitor.

* * * * *

```
                        SEQUENCE LISTING

<160> NUMBER OF SEQ ID NOS: 4

<210> SEQ ID NO 1
<211> LENGTH: 223
<212> TYPE: PRT
<213> ORGANISM: Homo sapiens

<400> SEQUENCE: 1

Gly Ser Met Gly Asp Thr Lys Glu Gln Arg Ile Leu Asn His Val Leu
1               5                   10                  15

Gln His Ala Glu Pro Gly Asn Ala Gln Ser Val Leu Glu Ala Ile Asp
            20                  25                  30

Thr Tyr Cys Glu Gln Lys Glu Trp Ala Met Asn Val Gly Asp Lys Lys
        35                  40                  45

Gly Lys Ile Val Asp Ala Val Ile Gln Glu His Gln Pro Ser Val Leu
    50                  55                  60

Leu Glu Leu Gly Ala Tyr Cys Gly Tyr Ser Ala Val Arg Met Ala Arg
65                  70                  75                  80

Leu Leu Ser Pro Gly Ala Arg Leu Ile Thr Ile Glu Ile Asn Pro Asp
                85                  90                  95

Cys Ala Ala Ile Thr Gln Arg Met Val Asp Phe Ala Gly Val Lys Asp
            100                 105                 110

Lys Val Thr Leu Val Val Gly Ala Ser Gln Asp Ile Ile Pro Gln Leu
        115                 120                 125

Lys Lys Lys Tyr Asp Val Asp Thr Leu Asp Met Val Phe Leu Asp His
    130                 135                 140

Trp Lys Asp Arg Tyr Leu Pro Asp Thr Leu Leu Leu Glu Glu Cys Gly
145                 150                 155                 160

Leu Leu Arg Lys Gly Thr Val Leu Leu Ala Asp Asn Val Ile Cys Pro
                165                 170                 175

Gly Ala Pro Asp Phe Leu Ala His Val Arg Gly Ser Ser Cys Phe Glu
            180                 185                 190

Cys Thr His Tyr Gln Ser Phe Leu Glu Tyr Arg Glu Val Val Asp Gly
        195                 200                 205

Leu Glu Lys Ala Ile Tyr Lys Gly Pro Gly Ser Glu Ala Gly Pro
    210                 215                 220

<210> SEQ ID NO 2
<211> LENGTH: 684
<212> TYPE: DNA
<213> ORGANISM: Homo sapiens

<400> SEQUENCE: 2
tctggatcca tgggtgacac caaggagcag cgcatcctga accacgtgct gcagcatgcg      60
gagcccggga acgcacagag cgtgctggag gccattgaca cctactgcga gcagaaggag     120
tgggccatga acgtgggcga caagaaaggc aagatcgtgg acgccgtgat tcaggagcac     180
```

```
cagccctccg tgctgctgga gctgggggcc tactgtggct actcagctgt gcgcatggcc      240
cgcctgctgt caccaggggc gaggctgatc accatcgaga tcaaccccga ctgtgccgcc      300
atcacccagc ggatggtgga tttcgctggc gtgaaggaca aggtcaccct tgtggttgga      360
gcgtcccagg acatcatccc ccagctgaag aagaagtatg atgtggacac actggacatg      420
gtcttcctcg accactggaa ggaccggtac ctgccggaca cgcttctctt ggaggaatgt      480
ggcctgctgc ggaaggggac agtgctactg gctgacaacg tgatctgccc aggtgcgcca      540
gacttcctag cacacgtgcg cgggagcagc tgctttgagt gcacacacta ccaatcgttc      600
ctggaataca gggaggtggt ggacggcctg gagaaggcca tctacaaggg cccaggcagc      660
gaagcagggc cctgagaatt ctct                                              684

<210> SEQ ID NO 3
<211> LENGTH: 27
<212> TYPE: DNA
<213> ORGANISM: Artificial Sequence
<220> FEATURE:
<223> OTHER INFORMATION: 5'-primer

<400> SEQUENCE: 3
tctggatcca tgggtgacac caaggag                                           27

<210> SEQ ID NO 4
<211> LENGTH: 28
<212> TYPE: DNA
<213> ORGANISM: Artificial Sequence
<220> FEATURE:
<223> OTHER INFORMATION: 3' primer

<400> SEQUENCE: 4
agagaattct cagggccctg cttcgctg                                          28
```